US012508116B2

(12) United States Patent
Greenhalgh et al.

(10) Patent No.: US 12,508,116 B2
(45) Date of Patent: Dec. 30, 2025

(54) IMPLANTS WITH CORNER-LOCK STITCH PATTERNS

(71) Applicant: TELA Bio, Inc., Malvern, PA (US)

(72) Inventors: Skott Greenhalgh, Gladwyne, PA (US); John-Paul Romano, Chalfont, PA (US)

(73) Assignee: TELA Bio, Inc., Malvern, PA (US)

( * ) Notice: Subject to any disclaimer, the term of this patent is extended or adjusted under 35 U.S.C. 154(b) by 0 days.

(21) Appl. No.: 18/967,461

(22) Filed: Dec. 3, 2024

(65) Prior Publication Data

US 2025/0090295 A1 Mar. 20, 2025

Related U.S. Application Data

(63) Continuation of application No. 18/511,680, filed on Nov. 16, 2023, now Pat. No. 12,208,000, which is a (Continued)

(51) Int. Cl.

| | |
|---|---|
| ***A61F 2/00*** | (2006.01) |
| ***D05B 1/12*** | (2006.01) |
| ***D05B 93/00*** | (2006.01) |

(52) U.S. Cl.

CPC .............. *A61F 2/0063* (2013.01); *D05B 1/12* (2013.01); *D05B 93/00* (2013.01); *A61F 2002/0068* (2013.01); *A61F 2220/0075* (2013.01)

(58) Field of Classification Search

CPC ......... D05B 1/12; D05B 93/00; A61F 2/0063; A61F 2002/0068; A61F 2002/0075

See application file for complete search history.

(56) References Cited

U.S. PATENT DOCUMENTS

| | | | |
|---|---|---|---|
| 2,259,025 A | 10/1941 | Cosgro |
| 3,033,139 A | 5/1962 | Tateishi |

(Continued)

FOREIGN PATENT DOCUMENTS

| | | | |
|---|---|---|---|
| DE | 10312674 A1 | 10/2003 |
| DE | 112007001732 T5 | 4/2011 |

(Continued)

OTHER PUBLICATIONS

Greenhalgh et al.; U.S. Appl. No. 19/009,833 entitled "Textured medical textiles,", filed Jan. 3, 2025.

(Continued)

*Primary Examiner* — Nathan E Durham
(74) *Attorney, Agent, or Firm* — Shay Glenn LLP

(57) ABSTRACT

Implants including stitching patterns that overlap to produce a corner-locked stitch pattern. An implant may include a substrate including a biocompatible material a reinforcing mesh sewn into the substrate. The reinforcing mesh may include a corner-stitch pattern that includes a first lock-stitch pattern and a second lock-stitch pattern. The first lock-stitch pattern may include a first upper thread and a first lower thread that interlace at a first thread interlace point. The second lock-stitch pattern may include a second upper thread and a second lower thread that interlace at a second thread interlace point. The second lock-stitch pattern may overlap the first lock-stitch pattern such that the second upper thread and the second lower thread envelop the first upper thread and the first lower thread adjacent to the first thread interlace point and the second thread interlace point.

20 Claims, 22 Drawing Sheets

Related U.S. Application Data continuation of application No. 17/710,671, filed on Mar. 31, 2022, now Pat. No. 11,864,987, which is a continuation of application No. 16/284,976, filed on Feb. 25, 2019, now Pat. No. 11,344,397, which is a continuation of application No. 15/196,439, filed on Jun. 29, 2016, now Pat. No. 10,213,284.

(60) Provisional application No. 62/186,437, filed on Jun. 30, 2015.

(56) References Cited

U.S. PATENT DOCUMENTS

| | | | |
|---|---|---|---|
| 3,054,406 | A | 9/1962 | Usher |
| 3,155,095 | A | 11/1964 | Brown |
| 3,364,200 | A | 1/1968 | Ashton et al. |
| 3,658,023 | A | 4/1972 | Rossi |
| 4,466,370 | A | 8/1984 | Eguchi et al. |
| 5,593,441 | A | 1/1997 | Lichtenstein et al. |
| 5,634,931 | A | 6/1997 | Kugel |
| 5,683,400 | A | 11/1997 | McGuire |
| 5,707,395 | A | 1/1998 | Li |
| 5,723,010 | A | 3/1998 | Yui et al. |
| 5,919,232 | A | 7/1999 | Chaffringeon et al. |
| 5,990,378 | A | 11/1999 | Ellis |
| 6,120,539 | A | 9/2000 | Eldridge et al. |
| 6,258,124 | B1 | 7/2001 | Darois et al. |
| 6,319,264 | B1 | 11/2001 | Törmäläet al. |
| 6,371,985 | B1 | 4/2002 | Goldberg |
| 6,383,201 | B1 | 5/2002 | Dong |
| 6,652,595 | B1 | 11/2003 | Nicolo |
| 6,814,748 | B1 | 11/2004 | Baker et al. |
| 6,962,120 | B1 | 11/2005 | Fujikura et al. |
| 7,824,420 | B2 | 11/2010 | Eldridge et al. |
| 7,946,236 | B2 | 5/2011 | Butcher |
| 8,074,591 | B2 | 12/2011 | Butcher et al. |
| 8,182,545 | B2 | 5/2012 | Cherok et al. |
| 8,236,342 | B2 | 8/2012 | Thomas et al. |
| 8,853,294 | B2 | 10/2014 | Myung et al. |
| 9,205,052 | B2 | 12/2015 | Kim et al. |
| 9,289,279 | B2 | 3/2016 | Wilson et al. |
| 9,295,757 | B2 | 3/2016 | Patel et al. |
| 9,326,840 | B2 | 5/2016 | Mortarino |
| 9,364,310 | B2 | 6/2016 | Stopek |
| 9,421,079 | B2 | 8/2016 | Koullick et al. |
| 9,468,705 | B2 | 10/2016 | Geller |
| 9,510,925 | B2 | 12/2016 | Hotter et al. |
| 9,554,887 | B2 | 1/2017 | Lecuivre |
| 9,585,838 | B2 | 3/2017 | Hartounian et al. |
| 9,770,414 | B2 | 9/2017 | Garcia et al. |
| 9,775,700 | B2 | 10/2017 | Greenhalgh et al. |
| 9,820,843 | B2 | 11/2017 | Greenhalgh et al. |
| 9,925,030 | B2 | 3/2018 | Greenhalgh et al. |
| 10,130,457 | B2 | 11/2018 | Greenhalgh et al. |
| 10,213,284 | B2 | 2/2019 | Greenhalgh et al. |
| 10,426,587 | B2 | 10/2019 | Greenhalgh et al. |
| 10,500,030 | B2 | 12/2019 | Greenhalgh et al. |
| 10,561,485 | B2 | 2/2020 | Greenhalgh et al. |
| 10,675,141 | B2 | 6/2020 | Greenhalgh et al. |
| 10,702,364 | B2 | 7/2020 | Greenhalgh et al. |
| 11,344,397 | B2 | 5/2022 | Greenhalgh et al. |
| 11,369,464 | B2 | 6/2022 | Greenhalgh et al. |
| 11,446,130 | B2 | 9/2022 | Greenhalgh et al. |
| 11,464,616 | B2 | 10/2022 | Greenhalgh et al. |
| 11,590,262 | B2 | 2/2023 | Greenhalgh |
| 11,628,054 | B2 | 4/2023 | Greenhalgh et al. |
| 11,864,987 | B2 | 1/2024 | Greenhalgh et al. |
| 12,016,972 | B2 | 6/2024 | Greenhalgh |
| 12,064,334 | B2 | 8/2024 | Greenhalgh et al. |
| 12,070,380 | B2 | 8/2024 | Greenhalgh et al. |
| 12,144,714 | B2 | 11/2024 | Greenhalgh et al. |
| 12,208,000 | B2 | 1/2025 | Greenhalgh et al. |
| 12,226,299 | B2 | 2/2025 | Greenhalgh et al. |
| 2001/0020188 | A1 | 9/2001 | Sander |
| 2002/0111392 | A1 | 8/2002 | Cruise |
| 2003/0023316 | A1 | 1/2003 | Brown et al. |
| 2003/0225355 | A1 | 12/2003 | Butler |
| 2004/0010320 | A1 | 1/2004 | Huckle et al. |
| 2004/0033212 | A1 | 2/2004 | Thomson et al. |
| 2004/0054376 | A1 | 3/2004 | Ory et al. |
| 2004/0078089 | A1 | 4/2004 | Ellis et al. |
| 2004/0138762 | A1 | 7/2004 | Therin et al. |
| 2004/0249457 | A1 | 12/2004 | Smith et al. |
| 2005/0070930 | A1 | 3/2005 | Kammerer |
| 2005/0113849 | A1 | 5/2005 | Popadiuk et al. |
| 2005/0113938 | A1 | 5/2005 | Jamiolkowski et al. |
| 2005/0118236 | A1 | 6/2005 | Qiu et al. |
| 2005/0255543 | A1 | 11/2005 | Just et al. |
| 2006/0178683 | A1 | 8/2006 | Shimoji et al. |
| 2006/0217747 | A1 | 9/2006 | Ferree |
| 2006/0229722 | A1 | 10/2006 | Bianchi et al. |
| 2007/0088434 | A1 | 4/2007 | Frank |
| 2007/0190108 | A1 | 8/2007 | Datta et al. |
| 2007/0224238 | A1 | 9/2007 | Mansmann et al. |
| 2007/0250147 | A1 | 10/2007 | Walther et al. |
| 2008/0097601 | A1 | 4/2008 | Codori-Hurff et al. |
| 2008/0167729 | A1 | 7/2008 | Nelson et al. |
| 2008/0178786 | A1* | 7/2008 | Butcher ................ A61F 2/0063 112/439 |
| 2008/0181928 | A1 | 7/2008 | Hakimi-Mehr et al. |
| 2009/0018655 | A1 | 1/2009 | Brunelle et al. |
| 2009/0054339 | A1 | 2/2009 | Marshall et al. |
| 2009/0069893 | A1 | 3/2009 | Paukshto et al. |
| 2009/0082864 | A1 | 3/2009 | Chen et al. |
| 2009/0149939 | A1 | 6/2009 | Godlewski et al. |
| 2009/0216338 | A1 | 8/2009 | Gingras et al. |
| 2009/0306688 | A1 | 12/2009 | Patel et al. |
| 2009/0326577 | A1 | 12/2009 | Johnson et al. |
| 2010/0010114 | A1 | 1/2010 | Myung et al. |
| 2010/0028396 | A1 | 2/2010 | Ward et al. |
| 2010/0063599 | A1 | 3/2010 | Brunelle et al. |
| 2010/0100107 | A1 | 4/2010 | Duggal et al. |
| 2010/0120679 | A1 | 5/2010 | Xu et al. |
| 2010/0217388 | A1 | 8/2010 | Cohen et al. |
| 2010/0249929 | A1 | 9/2010 | Kurz et al. |
| 2010/0254900 | A1 | 10/2010 | Campbell et al. |
| 2010/0305500 | A1 | 12/2010 | Lambert et al. |
| 2010/0311949 | A1 | 12/2010 | Akkus et al. |
| 2010/0318108 | A1 | 12/2010 | Datta et al. |
| 2010/0318124 | A1 | 12/2010 | Leung et al. |
| 2011/0014153 | A1 | 1/2011 | Derwin et al. |
| 2011/0020420 | A1 | 1/2011 | Bosley et al. |
| 2011/0125287 | A1 | 5/2011 | Hotter et al. |
| 2011/0196490 | A1 | 8/2011 | Gadikota et al. |
| 2011/0250264 | A1 | 10/2011 | Schutt et al. |
| 2011/0257761 | A1 | 10/2011 | Mortarino |
| 2011/0301717 | A1 | 12/2011 | Becker |
| 2012/0010637 | A1 | 1/2012 | Stopek et al. |
| 2012/0035608 | A1 | 2/2012 | Marchitto et al. |
| 2012/0082712 | A1 | 4/2012 | Stopek et al. |
| 2012/0095482 | A1 | 4/2012 | Peterson et al. |
| 2012/0143329 | A1 | 6/2012 | Kim |
| 2012/0165957 | A1 | 6/2012 | Everland et al. |
| 2012/0179176 | A1 | 7/2012 | Wilson et al. |
| 2012/0184974 | A1 | 7/2012 | Becker |
| 2012/0253464 | A1 | 10/2012 | Hwang et al. |
| 2013/0064772 | A1 | 3/2013 | Swiss et al. |
| 2013/0116799 | A1 | 5/2013 | Derwin et al. |
| 2013/0172994 | A1 | 7/2013 | Becker |
| 2013/0197300 | A1 | 8/2013 | Koullick et al. |
| 2013/0209547 | A1 | 8/2013 | Garcia et al. |
| 2013/0211307 | A1 | 8/2013 | Evans et al. |
| 2013/0267137 | A1 | 10/2013 | Peniston et al. |
| 2013/0303958 | A1 | 11/2013 | Holm et al. |
| 2013/0304098 | A1 | 11/2013 | Mortarino |
| 2013/0317286 | A1 | 11/2013 | Bluecher et al. |
| 2014/0090942 | A1 | 4/2014 | Schlipper |
| 2014/0094931 | A1 | 4/2014 | Derwin et al. |
| 2014/0276993 | A1 | 9/2014 | Reilly et al. |
| 2014/0364878 | A1 | 12/2014 | Ladet et al. |
| 2015/0112434 | A1 | 4/2015 | Felix et al. |
| 2015/0127103 | A1 | 5/2015 | Seedhom |
| 2015/0267330 | A1 | 9/2015 | Carrier et al. |
| 2015/0297798 | A1 | 10/2015 | Badylak et al. |

(56) References Cited

U.S. PATENT DOCUMENTS

| | | | |
|---|---|---|---|
| 2016/0058534 | A1 | 3/2016 | Derwin et al. |
| 2016/0058589 | A1 | 3/2016 | Bar et al. |
| 2016/0136289 | A1 | 5/2016 | Puri et al. |
| 2016/0206580 | A1 | 7/2016 | Los et al. |
| 2016/0262208 | A1 | 9/2016 | Hsieh |
| 2016/0374791 | A1 | 12/2016 | Lecuivre et al. |
| 2017/0027679 | A1 | 2/2017 | Serban et al. |
| 2017/0086972 | A1 | 3/2017 | Braido et al. |
| 2017/0245847 | A1 | 8/2017 | Obermiller et al. |
| 2019/0008623 | A1 | 1/2019 | Nemoto et al. |
| 2020/0360129 | A1 | 11/2020 | Moses et al. |
| 2021/0128793 | A1 | 5/2021 | Mongrain et al. |
| 2021/0290416 | A1 | 9/2021 | Hall et al. |
| 2021/0322666 | A1 | 10/2021 | Greener |
| 2022/0110749 | A1 | 4/2022 | Hariton et al. |
| 2022/0211367 | A1 | 7/2022 | Schmid et al. |
| 2023/0293281 | A1 | 9/2023 | Greenhalgh et al. |
| 2023/0338637 | A1 | 10/2023 | Nazerali et al. |
| 2024/0299628 | A1 | 9/2024 | Greenhalgh |
| 2024/0374367 | A1 | 11/2024 | Romano et al. |
| 2025/0041040 | A1 | 2/2025 | Greenhalgh et al. |
| 2025/0049552 | A1 | 2/2025 | Greenhalgh et al. |

FOREIGN PATENT DOCUMENTS

| | | | |
|---|---|---|---|
| EP | 2198854 | A2 | 6/2010 |
| EP | 2229918 | A1 | 9/2010 |
| EP | 2300066 | A2 | 3/2011 |
| EP | 2344133 | A2 | 7/2011 |
| JP | 2015025033 | A | 2/2015 |
| RU | 2524196 | C2 | 7/2014 |
| WO | WO00/57812 | A1 | 10/2000 |
| WO | WO02/078568 | A1 | 10/2002 |
| WO | WO03/082363 | A1 | 10/2003 |
| WO | WO03/094781 | A1 | 11/2003 |
| WO | WO2008/095038 | A1 | 8/2008 |
| WO | WO2012/017415 | A2 | 2/2012 |
| WO | WO2017/050837 | A1 | 3/2017 |
| WO | WO2017/191276 | A1 | 11/2017 |
| WO | WO2017/223462 | A1 | 12/2017 |

OTHER PUBLICATIONS

Deeken et al., Physiocomechanical evaluation of absorbable and nonabsorbable barrier composite meshes for laparoscopic ventral hernia repair. Surg. Endosc., 25(5), 1541-1552 ( 12 pages, Author Manuscript); May 2011.

Franklin et al.; Uptake of tetracycline by aortic aneurysm wall and its effect on inflammation and proteolysis; British Journal of Surgery; 86(6); pp. 771-775; Jun. 1999.

Mayo Clinic;Placement of Breast Implants; retrieved May 25, 2017 from http://www.mayoclinic.org/placement-of-breast-implants/img-20007384; 1 pg; May 25, 2017.

Pyo et al.; Targeted gene disruption of matrix metalloproteinase-9 (gelatinase B) suppresses development of experimental abdominal aortic aneurysms; The journal of Clinical Investigation; 105(11); pp. 1641-1649; Jun. 2000.

Tambiah et al.; Provocation of experimental aortic inflammation and dilatation by inflammatory mediators and chlamydia pneumoniae; British Journal of Surgery; 88(7); pp. 935-940; Jul. 2001.

Walton et al.; Inhibition of prostoglandin E2 synthesis in abdominal aortic; Circulation; 100; pp. 48-54, 8 pages; Jul. 1999.

Xu et al.; Sp1 increases expression of cyclooxygenase-2 in hypoxic vascular endothelium implications for the mechanisms of aortic aneurysm and heart failure; journal of Biological Chemistry; 275(32); pp. 24583-24589; Aug. 2000.

Nazerali; U.S. Appl. No. 17/447,166 entitled "Subcutaneous and pocket irrigator,", filed Sep. 8, 2021.

* cited by examiner

Clamped Test Sample with Ball

Test Sample in Ring Clamp – Section View

IMPLANTS WITH CORNER-LOCK STITCH PATTERNS

CROSS REFERENCE TO RELATED APPLICATIONS

This application is a continuation of U.S. patent application Ser. No. 18/511,680, titled "CORNER-LOCK STITCH PATTERNS," filed Nov. 16, 2023, now U.S. Patent Application Publication No. US-20240341939-A1, which is a continuation of U.S. patent application Ser. No. 17/710,671, titled "CORNER-LOCK STITCH PATTERNS," filed Mar. 31, 2022, now U.S. Pat. No. 11,864,987, which is a continuation of U.S. patent application Ser. No. 16/284,976, titled "CORNER-LOCK STITCH PATTERNS," filed on Feb. 25, 2019, now U.S. Pat. No. 11,344,397, which is a continuation of U.S. patent application Ser. No. 15/196,439, titled "CORNER-LOCK STITCH PATTERNS," filed on Jun. 29, 2016, now U.S. Pat. No. 10,213,284, which claims priority to U.S. Provisional Patent Application No. 62/186,437, titled "CORNER-LOCK STITCH PATTERNS," filed on Jun. 30, 2015, each of which is incorporated by reference herein in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The disclosure relates generally to the field of sewing. More particularly, the disclosure relates to corner-lock stitches made by overlaying threads of separately laid stitch patterns, with the overlays being supported by thread interlace points near to the overlay points. The disclosure further relates to methods for producing these corner-lock stitches, meshes formed from a plurality of interwoven corner-lock stitches, and substrate materials, including substrate meshes, comprising corner-lock stitch patterns. The corner-lock stitches resist deformation, stretching, and pulling apart of the stitch patterns. The corner-lock stitches can be used to modulate the compliance of a substrate, and can also be used to enhance the strength of a substrate.

BACKGROUND

Sewing is an ancient art, primarily used to join pieces of fabric or like materials together. Sewing may also be used to add designs onto (e.g., embroidery), or reinforce or add strength or rigidity to fabrics or like materials. Yarns or threads bridge pieces of materials together or form the design or reinforcing backbone in the materials.

Yarns or threads are placed via stitching, and stitching may be done by hand or by a machine. Various stitching techniques and patterns are available, depending on the particular application or the type of material.

The advent of the sewing machine introduced the lockstitch (FIG. 1A), whereby two separate threads (or yarns), an upper thread and lower thread, become intertwined by the coordination of the sewing needle, which delivers the upper thread into the material being sewn, and a secondary mechanism, typically a bobbin and bobbin driver, which provides the lower thread. The coordinated movement of the sewing needle and bobbin driver intertwines the upper and lower threads, which is known as a lockstitch, in the material being sewn.

Nearly any material that can be punctured with a sewing needle may be sewn. The materials may be woven, knitted, or non-woven. Historically, such materials included fabrics and textiles. In more recent times, materials have been expanded to include polymeric fabrics, as well as biotextiles and medical textiles. Biotextiles include implantable materials, including extracellular matrix scaffolds, prosthetic heart valves, synthetic skin, and other materials that include living tissue or materials derived from living tissue.

In some biotextiles, a reinforcing mesh may be sewn into the material. Medical practitioners have raised concerns, however, that in the event the biologic substrate material of the biotextiles is destroyed by the body, or resorbs too quickly (i.e., before the body self-repairs the injury for which the biotextile has been implanted), the wide voids/pores/interstices between stitch patterns in the extant reinforcing mesh may stretch open (FIG. 2), and allow body tissue to herniate through the stretched mesh cells, causing a potential serious condition in the patient. Accordingly, there is a need in the art to be able to prevent stretching and deformation of the pores of a sewn mesh, particularly for biotextiles.

SUMMARY

The disclosure features corner-lock stitch patterns, substrates comprising corner-lock stitch patterns, and methods for producing corner-lock stitch patterns or substrates comprising corner-lock stitch patterns. In some aspects, a corner-lock stitch pattern comprises a first pattern of a first upper thread and a first lower thread comprising one or more curves, one or more angles, or a combination of one or more curves and one or more angles, and a second pattern of a second upper thread and a second lower thread comprising one or more curves, one or more angles, or a combination of one or more curves and one or more angles. Yarn may be used in place of thread in the first pattern, second pattern, or both. At least one of the one or more curves or the one or more angles of the second pattern overlap at least one of the one or more curves or the one or more angles of the first pattern. One or more of the overlaps comprises a corner-lock stitch pattern comprising one or more thread interlace points and two or more thread overlays in which the second upper thread and second lower thread envelope the first upper thread and first lower thread. In preferred aspects, one or more of the overlaps comprises a corner-lock stitch pattern comprising two thread interlace points and two thread overlays in which the second upper thread and second lower thread envelope the first upper thread and first lower thread.

In some aspects, the first pattern and the second pattern each comprise one or more angles, and one or more of the overlaps comprises a corner-lock stitch pattern comprising one or more thread interlace points proximal to the vertex of each angle. In some aspects, the first pattern and the second pattern each comprise one or more angles, and one or more of the overlaps comprises a corner-lock stitch pattern comprising one or more thread interlace points in close proximity to the vertex of each angle. In some aspects, the first pattern and the second pattern each comprise one or more angles, and one or more of the overlaps comprises a corner-lock stitch pattern comprising one or more thread interlace points substantially at the vertex of each angle. In any such case, the two or more thread overlays may be proximal to the vertex, or may be in close proximity to the vertex, or may be substantially at the vertex.

The first pattern may comprises a plurality of angles forming one or more polygonal rings. The second pattern may comprise a plurality of angles forming one or more polygonal rings. At least one ring of the second pattern may overlap at least one ring of the first pattern, and each overlapping ring preferably comprises a corner-lock stitch pattern. The corner-lock stitch pattern may comprise one or more thread interlace points, which thread interlace points may be proximal to the vertex of overlapped angles from each overlapped ring, or may be in close proximity to the vertex of overlapped angles from each overlapped ring, or may be substantially at the vertex of overlapped angles from each overlapped ring. In any such case, the two or more thread overlays may be proximal to the vertex, or may be in close proximity to the vertex, or may be substantially at the vertex. The one or more polygonal rings may comprise substantially an irregular shape, or a diamond, square, rhomboid, rectangular, or parallelogram shape, or any combination thereof.

In some aspects, the first pattern and the second pattern each comprise one or more curves, and one or more of the overlaps comprises a corner-lock stitch pattern comprising one or more thread interlace points proximal to the vertex of each curve. In some aspects, the first pattern and the second pattern each comprise one or more curves, and one or more of the overlaps comprises a corner-lock stitch pattern comprising one or more thread interlace points in close proximity to the vertex of each curve. In some aspects, the first pattern and the second pattern each comprise one or more curves, and one or more of the overlaps comprises a corner-lock stitch pattern comprising one or more thread interlace points substantially at the vertex of each curve. In any such case, the two or more thread overlays may be proximal to the vertex, or may be in close proximity to the vertex, or may be substantially at the vertex.

The first pattern may comprise a plurality of curves forming one or more circular rings. The second pattern may comprise a plurality of curves forming one or more circular rings. At least one ring of the second pattern may overlap at least one ring of the first pattern, and each overlapping ring preferably comprises a corner-lock stitch pattern. The corner-lock stitch pattern may comprise a thread interlace point, which thread interlace point may be proximal to the vertex of the overlapped curve of each ring, or may be in close proximity to proximal to the vertex of the overlapped curve of each ring, or may be substantially at the vertex of the overlapped curve of each ring. In any such case, the two or more thread overlays may be proximal to the vertex, or may be in close proximity to the vertex, or may be substantially at the vertex.

Meshes comprising one or more corner-lock stitch patterns are provided. A plurality of corner-lock stitches together form a mesh.

Substrate materials comprising one or more corner-lock stitch patterns are provided. A corner-lock stitch pattern, or mesh thereof, is sewn or embroidered into or onto a substrate. The substrate itself may be a mesh. In some aspects, a substrate comprising a corner-lock stitch pattern sewn or embroidered onto or into the substrate comprises a hernia repair material. The substrate may comprise a polymer. The substrate may comprise a medical textile. The substrate may comprise a biotextile. The thread or yarn used to sew or embroider the corner-lock stitch pattern may comprise a polymer.

In a mesh comprising a plurality of corner-lock stitch patterns, the pores of the mesh, as bound by a plurality of corner-lock stitches, may have a substantially diamond shape, a square shape, a parallelogram shape, a rhomboid shape, or a combination thereof. The pores of the mesh may have substantially a hexagonal shape. The pores of the mesh may have a substantially octagonal shape. The pores of the mesh may have a substantially circular shape. The pores may be arranged in one or more rows, in any directional orientation. The pores may overlap other pores.

In some aspects, the methods comprise sewing a first upper thread and a first lower thread in a first pattern into a substrate material, wherein the first pattern comprises one or more curves, one or more angles, or a combination of one or more curves and one or more angles, then sewing a second upper thread and a second lower thread in a second pattern into the substrate material, wherein the second pattern comprises one or more curves, one or more angles, or a combination of one or more curves and one or more angles. Based on such pattern sewing, at least one of the one or more curves or the one or more angles of the second pattern overlaps at least one of the one or more curves or the one or more angles of the first pattern, and each overlap comprises a corner-lock stitch pattern comprising at least one thread interlace point substantially at the vertex of each curve, angle, or curve and angle, and two thread overlays proximal to each vertex. Each thread overlay comprises the second upper thread and second lower thread enveloping the first upper thread and first lower thread.

In some aspects of the methods, the first pattern and the second pattern each comprise one or more angles, and one or more of the overlaps comprises a corner-lock stitch pattern comprising one or more thread interlace points proximal to the vertex of each angle. In some aspects, the first pattern and the second pattern each comprise one or more angles, and one or more of the overlaps comprises a corner-lock stitch pattern comprising one or more thread interlace points in close proximity to the vertex of each angle. In some aspects, the first pattern and the second pattern each comprise one or more angles, and one or more of the overlaps comprises a corner-lock stitch pattern comprising one or more thread interlace points substantially at the vertex of each angle. In any such case, the two or more thread overlays may be proximal to the vertex, or may be in close proximity to the vertex, or may be substantially at the vertex.

The first pattern may comprises a plurality of angles forming one or more polygonal rings. The second pattern may comprise a plurality of angles forming one or more polygonal rings. At least one ring of the second pattern may overlap at least one ring of the first pattern, and each overlapping ring preferably comprises a corner-lock stitch pattern. The corner-lock stitch pattern may comprise one or more thread interlace points, which thread interlace points may be proximal to the vertex of overlapped angles from each overlapped ring, or may be in close proximity to the vertex of overlapped angles from each overlapped ring, or may be substantially at the vertex of overlapped angles from each overlapped ring. In any such case, the two or more thread overlays may be proximal to the vertex, or may be in close proximity to the vertex, or may be substantially at the vertex. The one or more polygonal rings may comprise substantially an irregular shape, or a diamond, square, rhomboid, rectangular, or parallelogram shape, or any combination thereof.

In some aspects of the methods, the first pattern and the second pattern each comprise one or more curves, and one or more of the overlaps comprises a corner-lock stitch pattern comprising one or more thread interlace points proximal to the vertex of each curve. In some aspects, the first pattern and the second pattern each comprise one or more curves, and one or more of the overlaps comprises a corner-lock stitch pattern comprising one or more thread interlace points in close proximity to the vertex of each curve. In some aspects, the first pattern and the second pattern each comprise one or more curves, and one or more of the overlaps comprises a corner-lock stitch pattern comprising one or more thread interlace points substantially at the vertex of each curve. In any such case, the two or more thread overlays may be proximal to the vertex, or may be in close proximity to the vertex, or may be substantially at the vertex.

The first pattern may comprise a plurality of curves forming one or more circular rings. The second pattern may comprise a plurality of curves forming one or more circular rings. At least one ring of the second pattern may overlap at least one ring of the first pattern, and each overlapping ring preferably comprises a corner-lock stitch pattern. The corner-lock stitch pattern may comprise a thread interlace point, which thread interlace point may be proximal to the vertex of the overlapped curve of each ring, or may be in close proximity to proximal to the vertex of the overlapped curve of each ring, or may be substantially at the vertex of the overlapped curve of each ring. In any such case, the two or more thread overlays may be proximal to the vertex, or may be in close proximity to the vertex, or may be substantially at the vertex.

In some aspects, the methods comprise sewing a first upper thread and a first lower thread in a first pattern into a substrate material, wherein the first pattern comprises one or more curves, one or more angles, or a combination of one or more curves and one or more angles, then sewing a second upper thread and a second lower thread in a second pattern into the substrate material, wherein the second pattern comprises one or more curves, one or more angles, or a combination of one or more curves and one or more angles. Based on such pattern sewing, at least one of the one or more curves or the one or more angles of the second pattern overlaps at least one of the one or more curves or the one or more angles of the first pattern, and each overlap comprises a corner-lock stitch pattern comprising one or more thread interlace points and two or more thread overlays. Each thread overlay comprises the second upper thread and second lower thread enveloping the first upper thread and first lower thread. In some aspects, the first pattern comprises a plurality of angles forming one or more polygonal rings, and the second pattern comprises a plurality of angles forming one or more polygonal rings. In such patterns, at least one ring of the second pattern overlaps at least one ring of the first pattern, and at least one of the overlapping rings comprises a corner-lock stitch pattern comprising more than one thread interlace point.

In some aspects, the methods comprise sewing a first upper thread and a first lower thread in a first pattern into a substrate material, wherein the first pattern comprises one or more straight lines, then sewing a second upper thread and a second lower thread in a second pattern into the substrate material, wherein the second pattern comprises a plurality of angles forming one or more polygonal rings. Based on such sewing patterns, at least one ring of the second pattern overlaps at least one of the straight lines of the first pattern and each overlap comprises a corner-lock stitch pattern comprising one or more thread interlace points and two or more thread overlays. Each thread overlay comprises the second upper thread and second lower thread enveloping the first upper thread and first lower thread. In some aspects, at least one of the polygonal rings comprises a corner-lock stitch pattern comprising more than one thread interlace point.

Such methods may be used to form a mesh comprising one or more corner-lock stitch patterns. Such methods may be used to impart one or more corner-lock stitch patterns, including a mesh comprising such patterns, into a substrate. The substrate may comprise a polymer. The substrate may comprise a medical textile. The substrate may comprise a biotextile. The thread or yarn used to sew or embroider the corner-lock stitch pattern may comprise a polymer. The mesh and/or substrate material may be biocompatible, and may be resorbable. The mesh and/or substrate material may comprise a hernia repair implant.

BRIEF DESCRIPTION OF THE DRAWINGS

According to common practice, the various features of the drawings are not to scale. On the contrary, the dimensions of the various features are arbitrarily expanded or reduced for clarity. Included in the drawings are the following figures.

DETAILED DESCRIPTION

Various terms relating to aspects of the disclosure are used throughout the specification and claims. Such terms are to be given their ordinary meaning in the art, unless otherwise indicated. Other specifically defined terms are to be construed in a manner consistent with the definition provided herein.

As used herein, the singular forms “a,” “an,” and “the” include plural referents unless expressly stated otherwise.

As used herein, the terms “first” and “second” do not necessarily have a temporal relationship. For example, a “second pattern” does not necessarily require that the “second pattern” be sewn after the “first pattern” is sewn. These terms generally include a positional relationship, for example, they may designate that there are two separate patterns that are sewn.

Figure 1A:
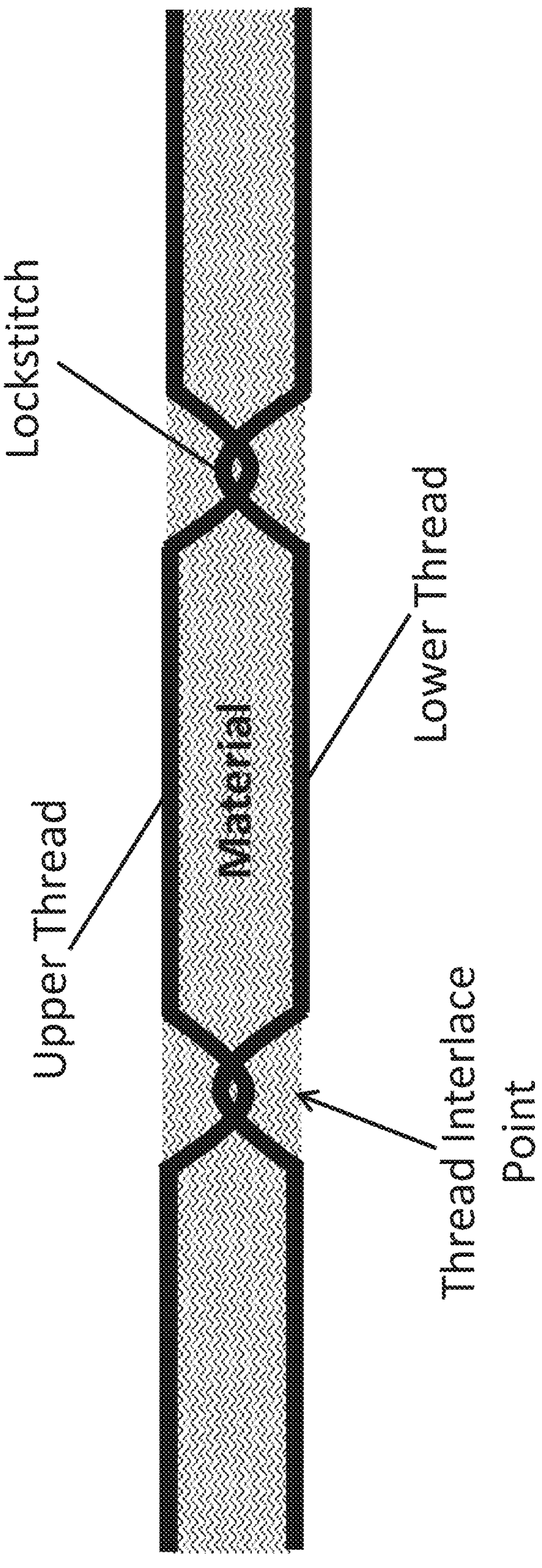
FIG. 1A shows an example of a typical lockstitch, having intertwined upper and lower threads. A typical lockstitch as shown may be present in a thread interlace point within a sewing pattern.
Figure 1B:
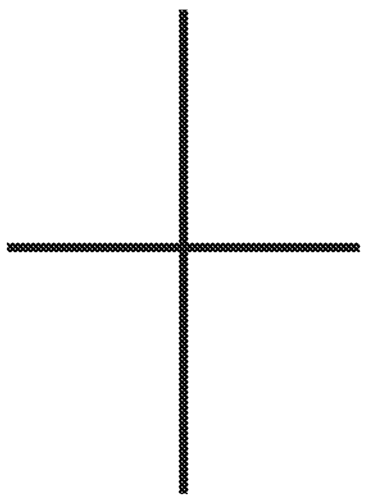
FIG. 1B shows an example of a stitch pattern in which two straight stitches intersect.

A “thread interlace point” includes a region where a top thread and a bottom thread are intertwined together. This may include, for example, a standard lock stitch (e.g., FIG. 1A). The top and bottom thread may be separate threads, or may be from the same continuous thread. By way of example, but not of limitation, a thread interlace point may be formed where a sewing needle punctures a substrate material or, if the substrate material comprises a mesh, the thread interlace point may be formed where a sewing needle passes through a pore of the mesh.

A polygon includes shapes comprised of at least angles and vertices, and sides with at least a straight segment at the angle/vertex. The polygon may comprise a regular or irregular shape. A "polygonal ring" comprises a closed polygon.

A "circular ring" includes a closed circle, sphere, oval, ellipse, O-shape, and other shapes comprising rounded sides.

Figure 6:
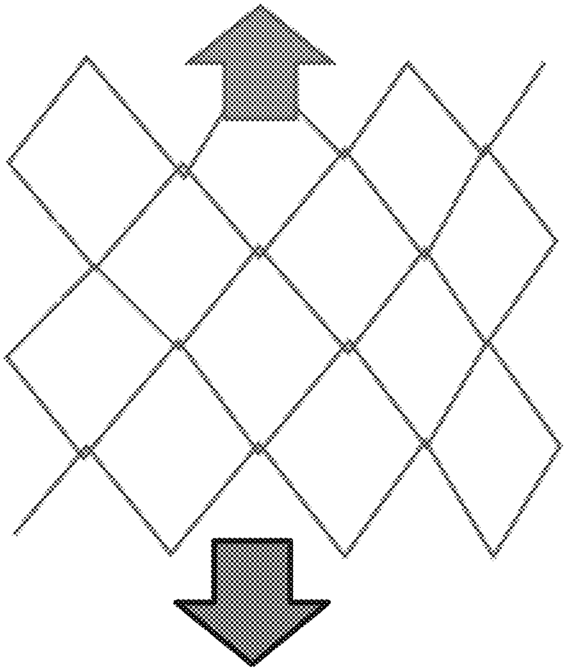
FIG. 6 shows an example of the mesh comprising corner-lock stitches placed under lateral tension (e.g., the mesh being pulled in the direction of each arrow). The corner-locked pores do not substantially deform, and the diamond shape is substantially maintained under tension.

It has been observed in accordance with the disclosure that stitching patterns can be overlaid in a way that produces a locked junction of threads. A plurality of inter-connected corner-locked stitch patterns may be used to produce a mesh. The corner-lock stitches resist puncture and deformation of the mesh (FIG. 12, parts A-C), such that the mesh pores substantially retain their original shape when challenged by a puncture force or by tension in any direction or combination of directions (FIG. 6). A mesh formed from corner-locked stitches may be used as a stand-alone textile resembling a knitted or woven fabric, or may be used as a strengthening, reinforcing, stabilizing, stiffening, or compliance-control pattern sewn or embroidered into or onto a material substrate (e.g., a biotextile, medical textile, or fabric), which substrate material itself may comprise a mesh (e.g., a mesh substrate). Thus, a corner-lock stitch pattern may be used to increase or decrease the level of compliance of, or modulate the directional compliance of a substrate into which the pattern is sewn. A corner-lock stitch pattern may also be used to increase the strength of a substrate into which the pattern is sewn. The mesh and its underlying stitch patterns may be customizable. Accordingly, the disclosure features corner-lock stitch patterns, meshes comprising such stitches, substrates comprising corner-lock stitch patterns or corner-locked meshes, and methods for producing such stitch patterns, meshes, and substrates.

In a first aspect, the disclosure provides methods for producing corner-lock stitches. Corner-lock stitches comprise interlocking stitch patterns. Corner-lock stitches are preferably created by sewing or embroidering, though in some aspects may be created by weaving, knitting, or warp knitting, and other suitable techniques. Sewing may be by machine or by hand, or by a combination thereof. Sewing may be with a ballpoint needle.

It is highly preferred that the stitching patterns are formed using at least two threads, with one such thread constituting an upper thread and the other thread constituting a lower thread. In some aspects, the stitching patterns may be formed using a single thread, which may be configured in a way to constitute both the upper and lower threads sewn into a pattern. The stitching pattern may be sewn into any configuration, including a regular or irregular, or variable configuration, including combinations or hybrids thereof. It is preferred that corner-lock stitches are produced from continuous sewing, though the corner-lock stitches may be produced from discontinuous sewing. For example, continuous sewing may comprise sewing the first pattern and sewing subsequent patterns without cutting the thread(s). Discontinuous sewing may comprise sewing the first pattern and sewing a subsequent pattern, but cutting the thread(s) at some point before sewing a subsequent pattern, or otherwise between subsequent patterns. In all cases, a yarn or filament may be used in place of thread.

Figure 7:
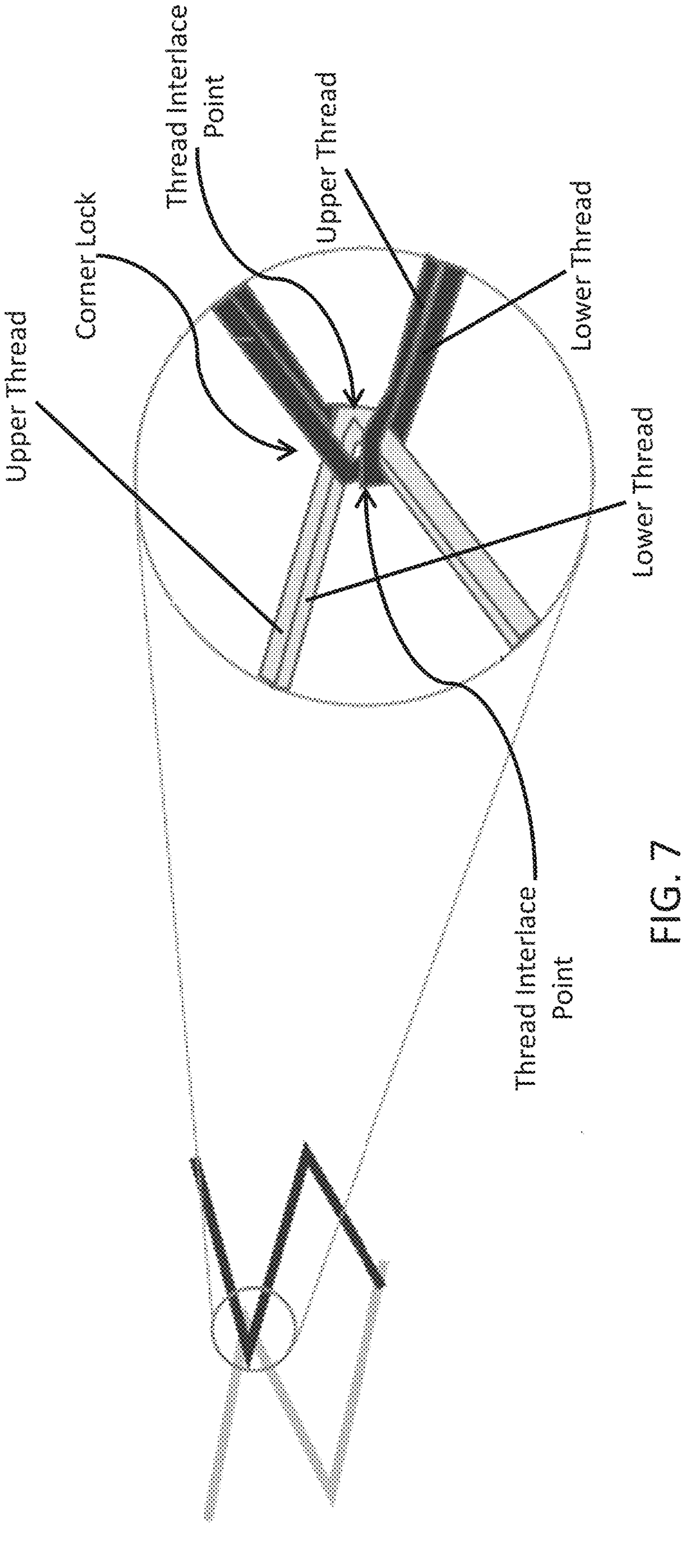
FIG. 7 shows a representation of a perspective of a corner-lock stitch, with the lighter grey line illustrating the first stitch pattern and the darker grey line illustrating the second stitch pattern. The expanded view (circle) shows a representation of the configuration of the upper and lower threads at the vertex of the overlapping thread pattern angles. As shown in the expanded view, the upper and lower thread of the second stitch pattern envelope the upper and lower thread of the first stich pattern near the vertex. As the second stitch pattern is laid, the sewing needle punctures the substrate material adjacent to the vertex of the first stitch pattern, creating a thread interlace point, but the upper and lower threads of the second stitch pattern encircle the upper and lower threads of the first stitch pattern in the process (a first overlay). As the sewing needle moves away to the next puncture point/interlace point in the material along the second stitch pattern, the upper and lower threads of the second stitch pattern again envelope the upper and lower threads of the first stitch pattern (a second overlay). This, in turn, creates the corner lock stitch.

In some aspects, the methods comprise sewing a first upper thread and a first lower thread in a first pattern into a substrate material, which first pattern comprises one or more curves, one or more angles, or a combination of one or more curves and one or more angles, then sewing a second upper thread and a second lower thread in a second pattern into the substrate material, which second pattern comprises one or more curves, one or more angles, or a combination of one or more curves and one or more angles. Sewing the second pattern allows at least one of the one or more curves or the one or more angles of the second pattern to overlap at least one of the one or more curves or the one or more angles of the first pattern. One or more such overlaps, in turn, comprise a corner-lock stitch pattern comprising at least one thread interlace point proximal to, in close proximity to, or substantially at the vertex of each curve, angle, or curve and angle, and two thread overlays proximal to, in close proximity to, or substantially at each vertex, and with each overlay comprising the second upper thread and second lower thread enveloping the first upper thread and first lower thread. An example is illustrated in FIG. 3, FIG. 4A, FIG. 4B, and FIG. 4C. In some aspects, a thread overlay includes the first upper and first lower thread being sandwiched between the second upper thread and the second lower thread (e.g., FIG. 7). A yarn or filament may be used in place of thread.

Figure 4B:
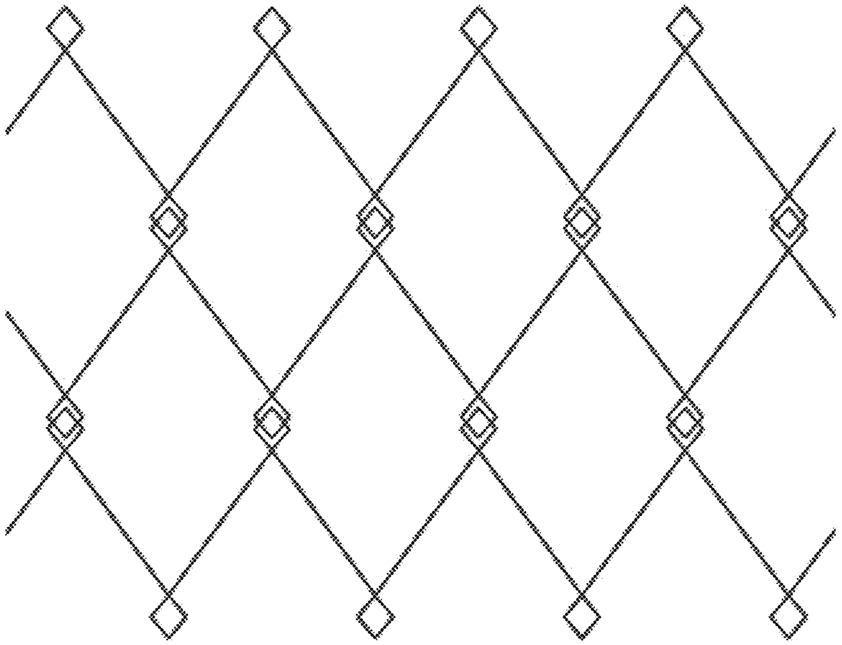
FIG. 4B shows an example of another corner-lock stitch pattern in which stitching patterns include a plurality of angles, some of which are formed into polygonal rings (shown for illustration purposes only in a diamond shape). The polygonal rings of separate stitch patterns overlap, establishing the corner-lock within the area of overlap, with the corner-lock including a thread interlace point from each thread pattern and two thread overlays. The corner-lock stitch pattern forms a mesh.
Figure 4A:
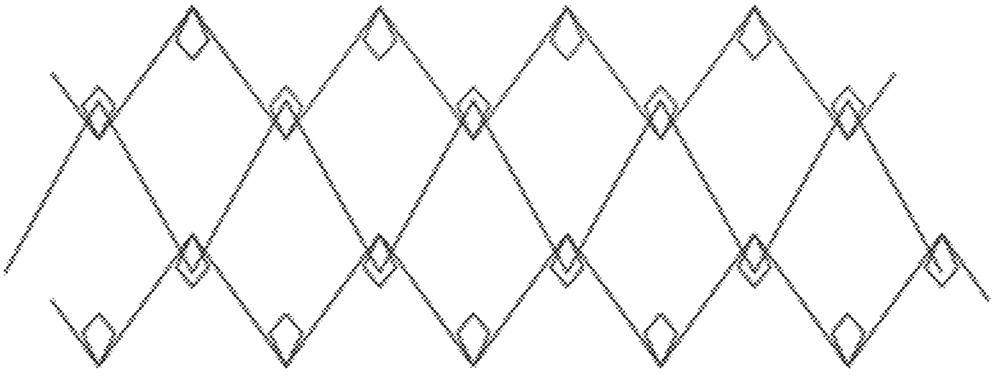
FIG. 4A shows an example of another corner-lock stitch pattern in which stitching patterns include a plurality of angles, some of which are formed into polygonal rings (shown for illustration purposes only in a diamond shape). The polygonal rings of separate stitch patterns overlap, establishing the corner-lock within the area of overlap, with the corner-lock including a thread interlace point from each thread pattern and two thread overlays. The corner-lock stitch pattern forms a mesh.
Figure 4C:
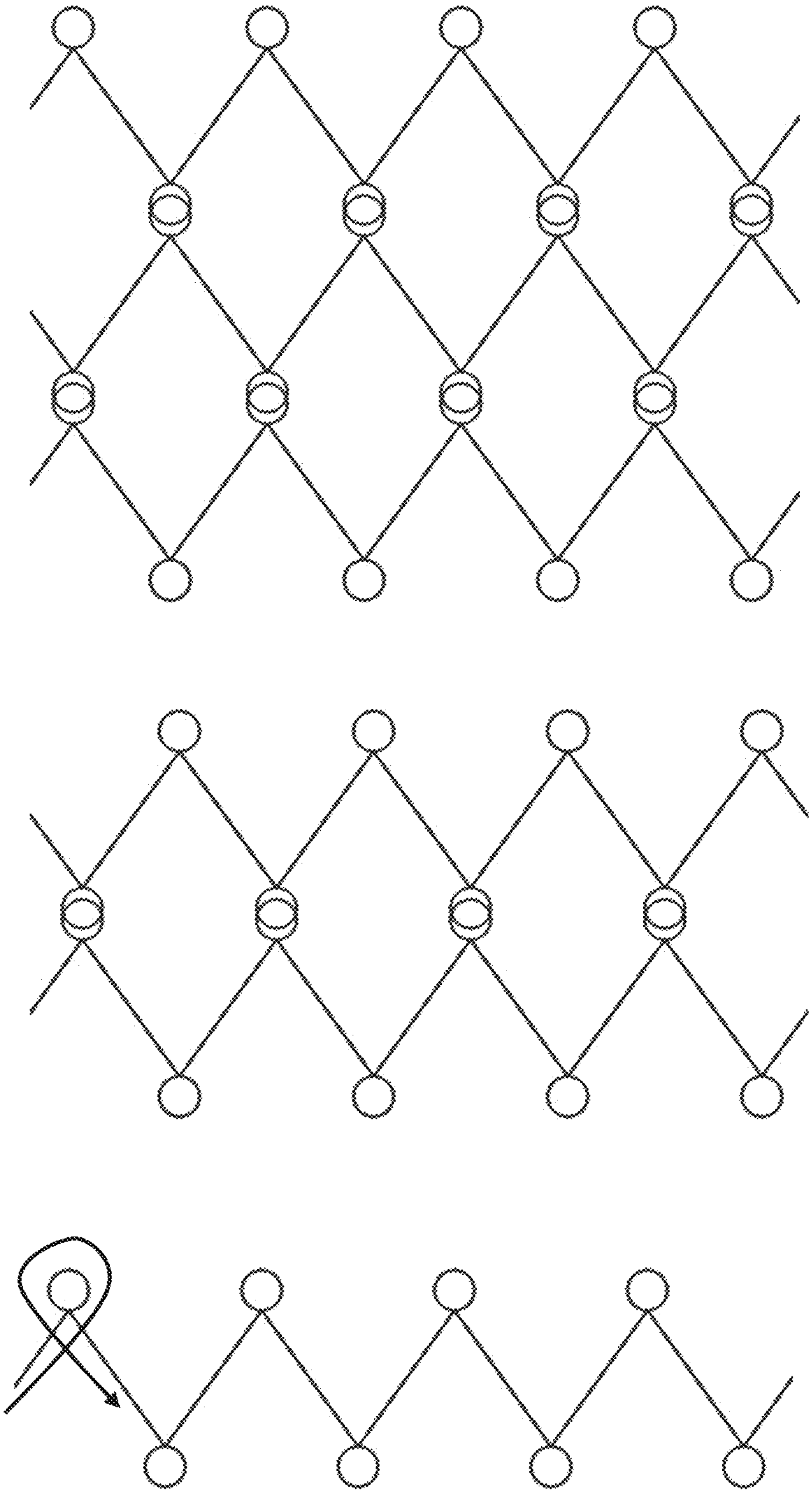
FIG. 4C shows an example of another corner-lock stitch pattern in which stitching patterns include a plurality of curves, some of which are formed into circular rings. The rings of separate stitch patterns overlap, establishing the corner-lock within the area of overlap, with the corner-lock including a thread interlace point from each thread pattern and two thread overlays. The corner-lock stitch pattern forms a mesh.

In some detailed aspects, the first pattern comprises a plurality of curves forming one or more circular rings, and the second pattern comprises a plurality of curves forming one or more circular rings (e.g., FIG. 4C). In such aspects, at least one ring of the second pattern overlaps at least one ring of the first pattern, and each overlapping ring comprises a corner-lock stitch pattern comprising a thread interlace point proximal to, in close proximity to, or substantially at the vertex of the overlapped curve of each ring and two thread overlays proximal to, in close proximity to, or substantially at each vertex, with each overlay comprising the second upper thread and second lower thread enveloping the first upper thread and first lower thread.

In some detailed aspects, the first pattern comprises a plurality of angles forming one or more polygonal rings, and the second pattern comprises a plurality of angles forming one or more polygonal rings (e.g., FIG. 4A and FIG. 4B). In such aspects, at least one ring of the second pattern overlaps at least one ring of the first pattern, and each overlapping ring comprises a corner-lock stitch pattern comprising at least one thread interlace point proximal to, in close proximity to, or substantially at the vertex of overlapped angles from each ring and two thread overlays proximal to, in close proximity to, or substantially at each vertex, with each overlay comprising the second upper thread and second lower thread enveloping the first upper thread and first lower thread. More than one interlace point may be included, for example, two, three, four, five, six, seven, eight, nine, ten, or more than ten interlace points may be included.

In some aspects, the methods comprise sewing a first upper thread and a first lower thread in a first pattern into a substrate material, which first pattern comprises one or more curves, one or more angles, or a combination of one or more curves and one or more angles, then sewing a second upper thread and a second lower thread in a second pattern into the substrate material, which second pattern comprises one or more curves, one or more angles, or a combination of one or more curves and one or more angles. Sewing the second pattern allows at least one of the one or more curves or the one or more angles of the second pattern to overlap at least one of the one or more curves or the one or more angles of the first pattern. One or more overlaps comprise a corner-lock stitch pattern comprising one or more thread interlace points and two or more thread overlays, each overlay comprising the second upper thread and second lower thread enveloping the first upper thread and first lower thread. See, FIG. 3, FIG. 4A, FIG. 4B, and FIG. 4C. A yarn or filament may be used in place of thread. More than one interlace point may be included, for example, two, three, four, five, six, seven, eight, nine, ten, or more than ten interlace points may be included. More than one thread overlay may be included, for example, two, three, four, five, six, seven, eight, nine, ten, or more than ten overlays may be included.

In some detailed aspects, the first pattern comprises a plurality of angles forming one or more polygonal rings, and the second pattern comprises a plurality of angles forming one or more polygonal rings, wherein at least one ring of the second pattern overlaps at least one ring of the first pattern, and at least one of the overlapping rings comprises a corner-lock stitch pattern comprising more than one thread interlace point (e.g., FIG. 4A and FIG. 4B). More than one thread overlay may be included, for example, two, three, four, five, six, seven, eight, nine, ten, or more than ten overlays may be included.

Figure 5A:
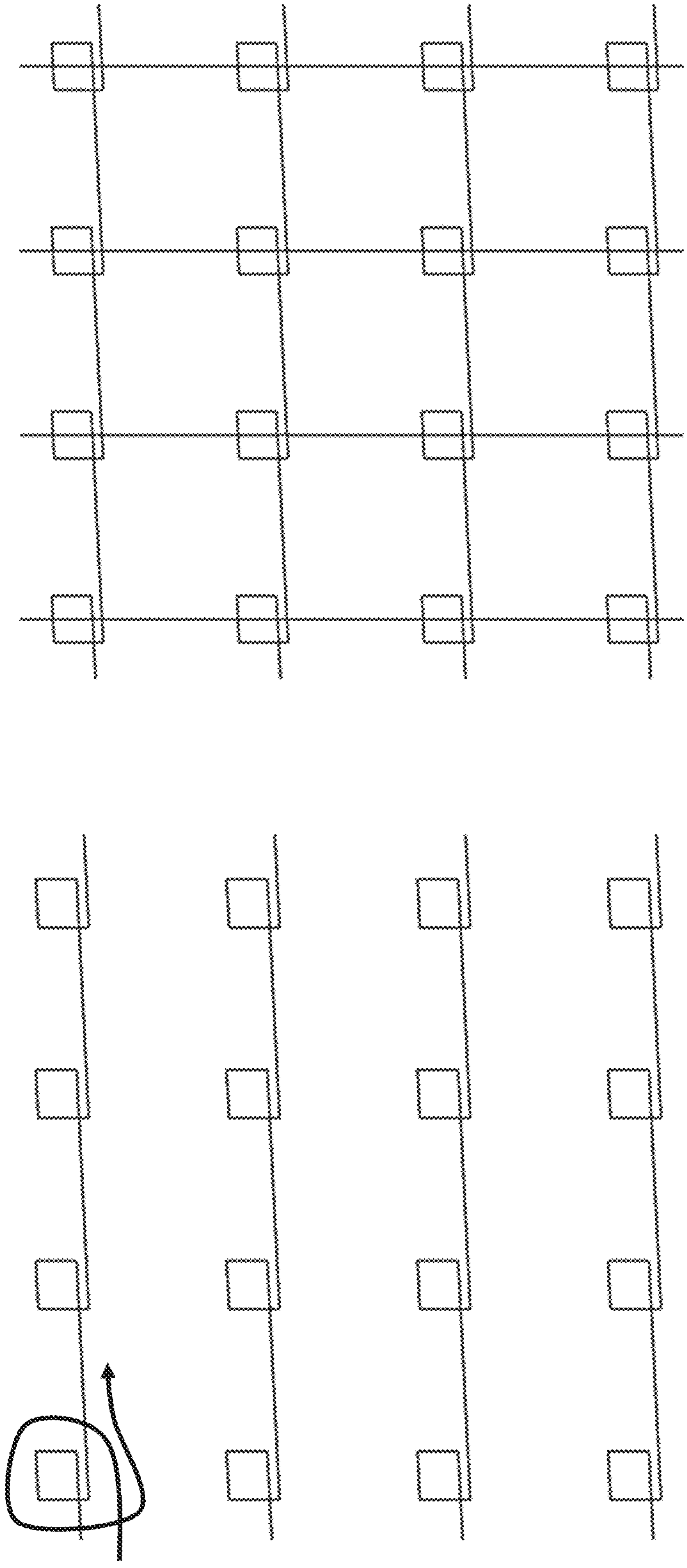
FIG. 5A shows an example of another corner-lock stitch pattern in which a stitching pattern of polygonal shapes is overlapped with a straight stitch pattern, establishing the corner-lock within the area of overlap, with the corner-lock including three thread overlays. The corner-lock stitch pattern forms a mesh.
Figure 5B:
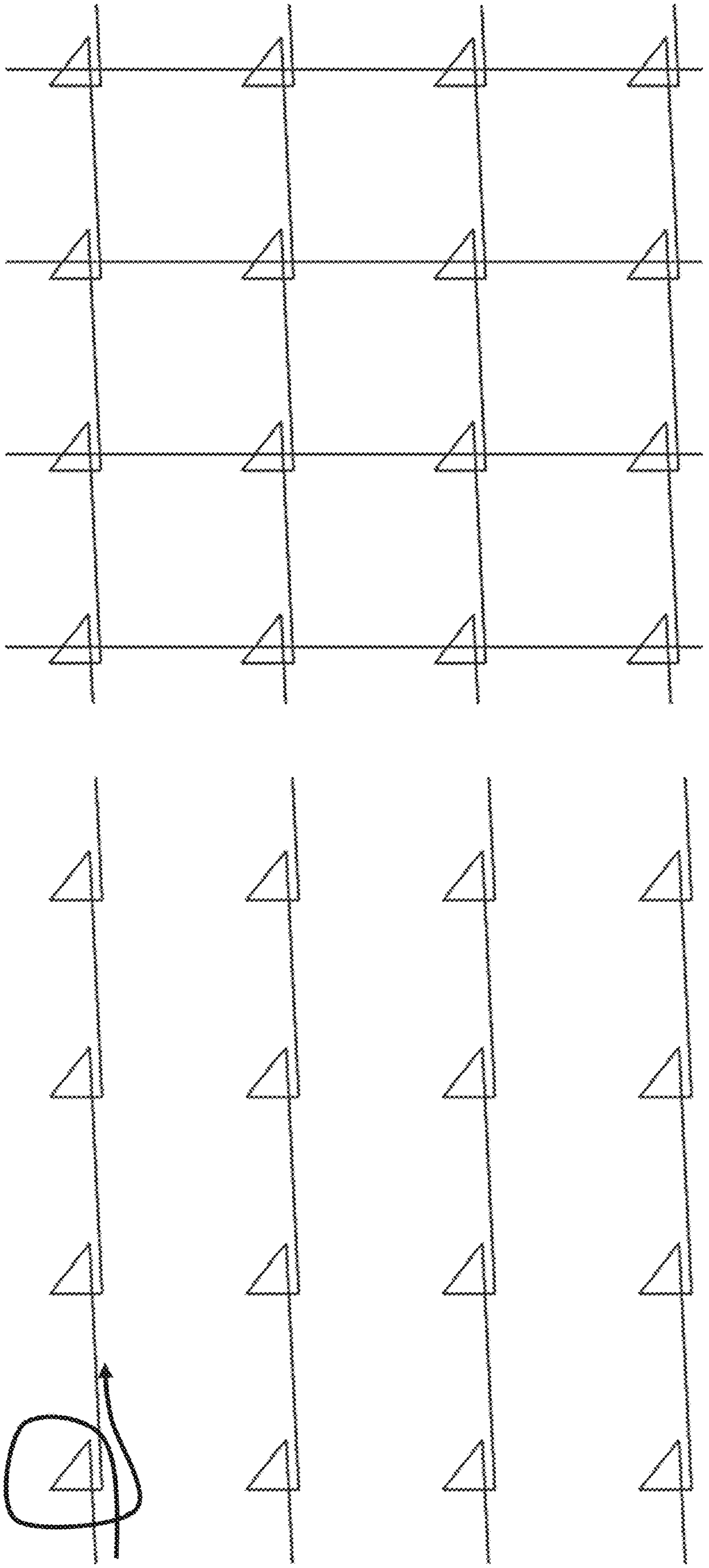
FIG. 5B shows an example of another corner-lock stitch pattern in which a stitching pattern of triangular shapes is overlapped with a straight stitch pattern, establishing the corner-lock within the area of overlap, with the corner-lock including three thread overlays. The corner-lock stitch pattern forms a mesh.
Figure 5C:
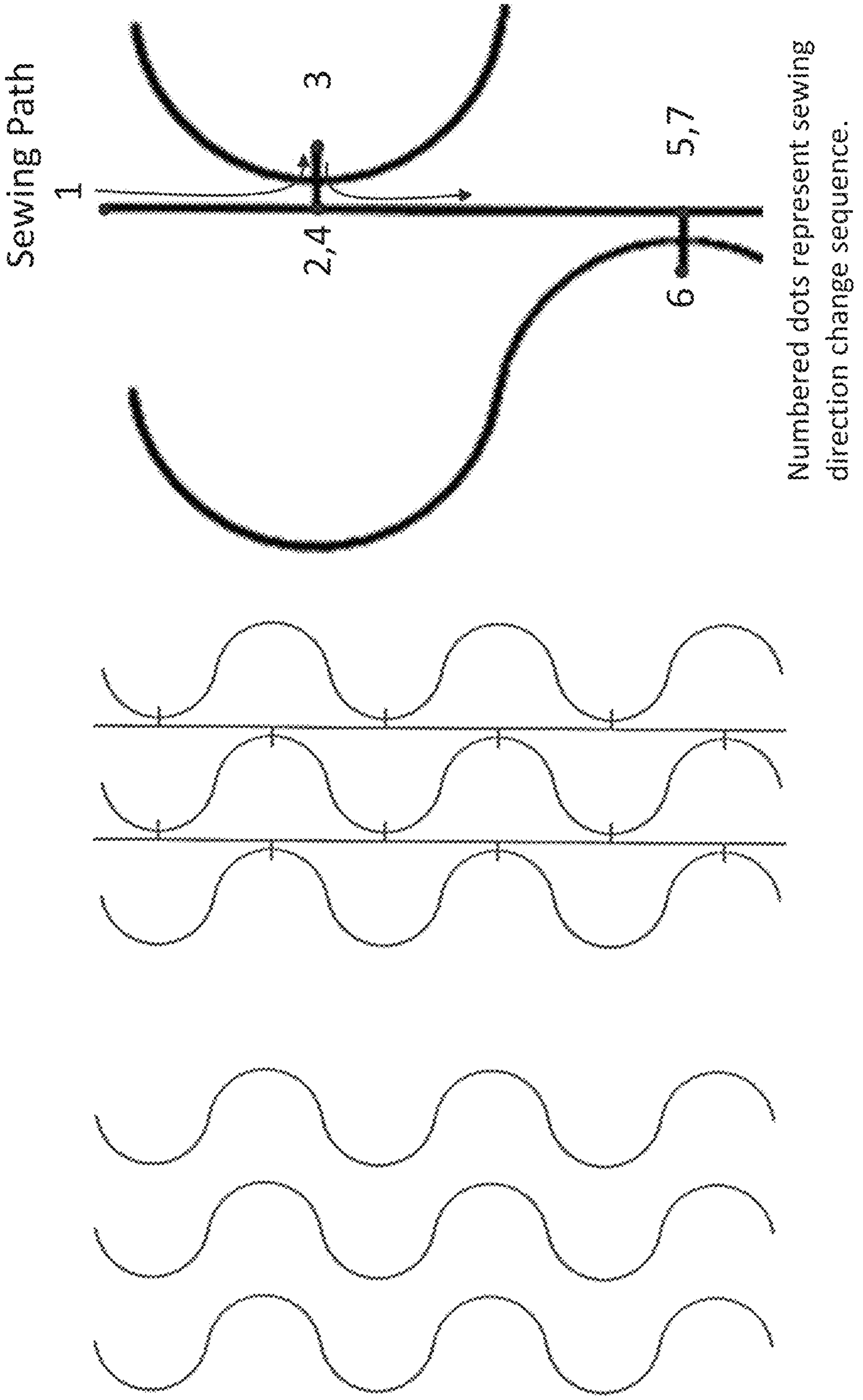
FIG. 5C shows an example of another corner-lock stitch pattern in which a curved stitched pattern is overlapped with a straight stitch pattern.

In some aspects, the methods comprise sewing a first upper thread and a first lower thread in a first pattern into a substrate material, which first pattern comprises one or more straight lines, then sewing a second upper thread and a second lower thread in a second pattern into the substrate material, which second pattern comprises a plurality of curves or angles forming one or more polygonal rings. Sewing the second pattern allows at least one ring of the second pattern to overlap at least one of the straight lines of the first pattern and each overlap comprises a corner-lock stitch pattern comprising one or more thread interlace points and two or more thread overlays, each overlay comprising the second upper thread and second lower thread enveloping the first upper thread and first lower thread. A yarn or filament may be used in place of thread. More than one interlace point may be included, for example, two, three, four, five, six, seven, eight, nine, ten, or more than ten interlace points may be included. More than one thread overlay may be included, for example, two, three, four, five, six, seven, eight, nine, ten, or more than ten overlays may be included. In some detailed aspects, at least one of the polygonal rings comprises a corner-lock stitch pattern comprising more than one thread interlace point. An example is illustrated in in FIG. 5A, FIG. 5B, and FIG. 5C.

Where polygonal rings or circular rings present, the ring is preferably sewn into the substrate material. In this respect, the ring is affixed to the substrate material, for example, via standard lockstitches about the ring perimeter and, thus, is distinct from a free-floating thread loop such as a loop stitch.

Corner-lock stitch patterns produced by any of the methods described herein are also provided. Meshes comprising one or more corner-lock stitch patterns produced by any of the methods described herein are also provided (a mesh may include any combination of corner-lock stitch patterns; the mesh need not be homogeneous in terms of the type of its underlying corner-lock stitch pattern). Substrates comprising one or more corner-lock stitch patterns produced by any of the methods described herein are also provided. Substrates comprising a mesh comprising one or more corner-lock stitch patterns produced by any of the methods described herein are also provided A plurality of corner-lock stitches may be used in combination to create a mesh or a net. Such a mesh or net may be a stand-alone material (e.g., not sewn or embroidered onto or into any other material). In some aspects, the mesh is sewn or embroidered onto or into a substrate. In this respect, the mesh may serve to impart design, strength, stiffness/rigidity, and/or reinforcement into the substrate. In some aspects, the substrate material may be removed or eliminated to leave the mesh as a stand-alone product. For example, the substrate material may be dissolvable, and may be dissolved following sewing or embroidering of the mesh in order to leave the corner-locked mesh behind. The mesh and substrate material may be separated from each other by any suitable technique in order to isolate the mesh.

Figure 2:
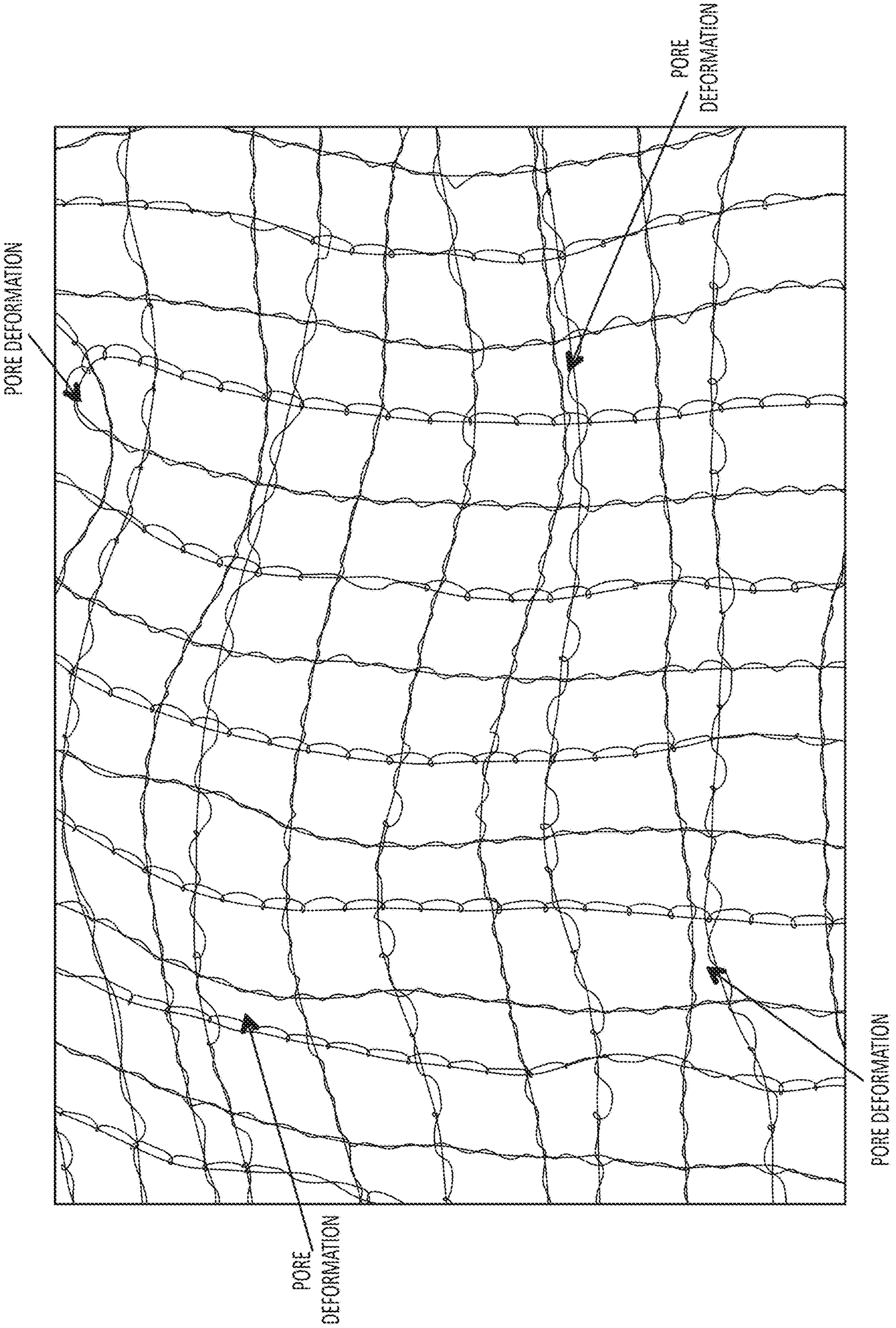
FIG. 2 shows an image of a mesh formed by overlapping straight stitches, where there is no corner-lock at intersecting points. The lack of a corner-lock causes individual pores or clusters of pores within the mesh to stretch and deform. Arrows show examples of such deformations, including widening, narrowing, and mis-shaping of the square/rectangular form originally produced by the overlapping of straight stitch patterns.
Figure 3:
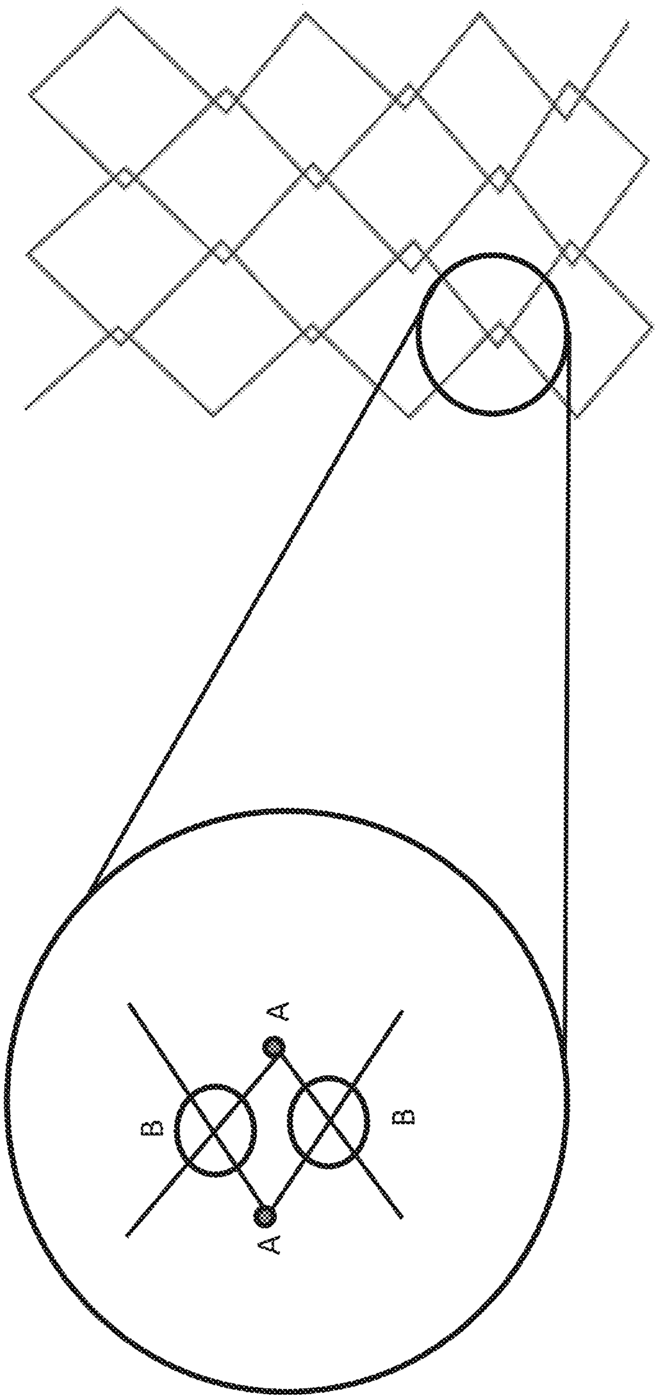
FIG. 3 shows an example of a corner-lock stitch pattern. This corner-lock includes a thread interlace point from each thread pattern (shown in the expanded view (circle) as points A), and two thread overlays (shown in the expanded view as points B). The corner-lock stitch pattern forms a mesh.
Figure 12:
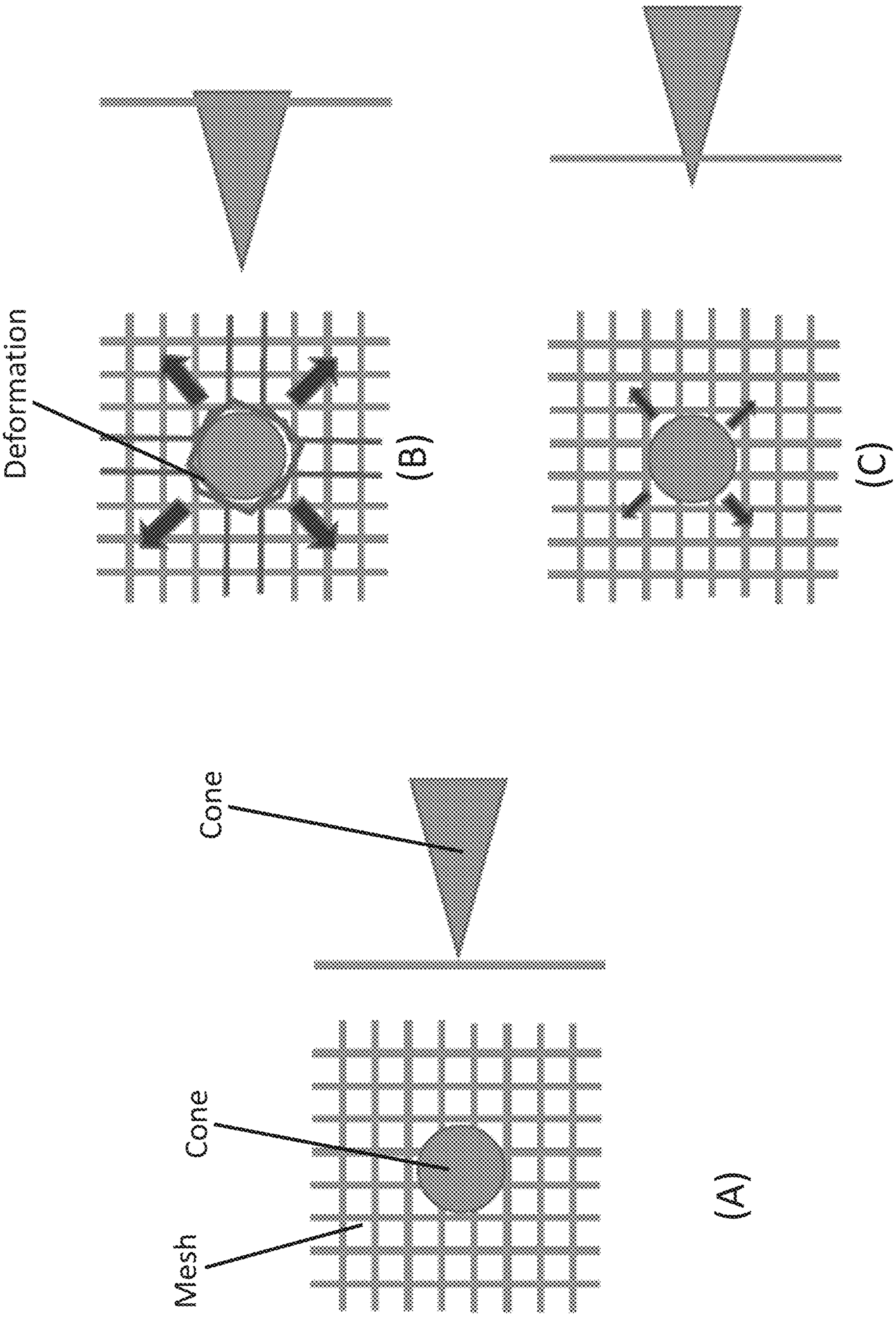
FIG. 12 shows a representation of puncture forces on a sewn mesh. In part A, a cone (the triangle) is pointed down through the horizontal plane of the mesh (represented by the circle), with the pointed tip of the cone placed in contact with the mesh in an attempt to push the cone through the mesh. Part B represents a non-corner-locked mesh produced by overlapping straight stitches. In part B, the cone is easily pushed into the mesh, causing the threads to spread apart and deform. Part C represents a corner-locked mesh according to this disclosure. In part C, the mesh resists puncture by the cone, and the threads do not spread apart or deform.

In any case, the pores of the mesh, being surrounded by corner-locked stitches substantially resist deformation via puncture (FIG. 12, part C), and substantially resist deformation via tension (FIG. 6). By way of example, FIG. 6 shows a representation of a corner-locked mesh, with tension being applied by pulling the mesh in the direction of the arrows. But the corner-lock stitches inhibit substantial widening of the pores in the direction of the tension (as shown in FIG. 6, the tension being applied along a horizontal axis) and inhibit substantial narrowing of the pores in directions other than the direction of the tension (e.g., per FIG. 6, a vertical axis). The corner-locked meshes also resist deformation from vertical tension, or tension from multiple directions, including simultaneous vertical and horizontal tension. This stands in contrast to the deformation caused by puncture or tension as shown in FIG. 12, part B and in FIG. 2.

Figure 8A:
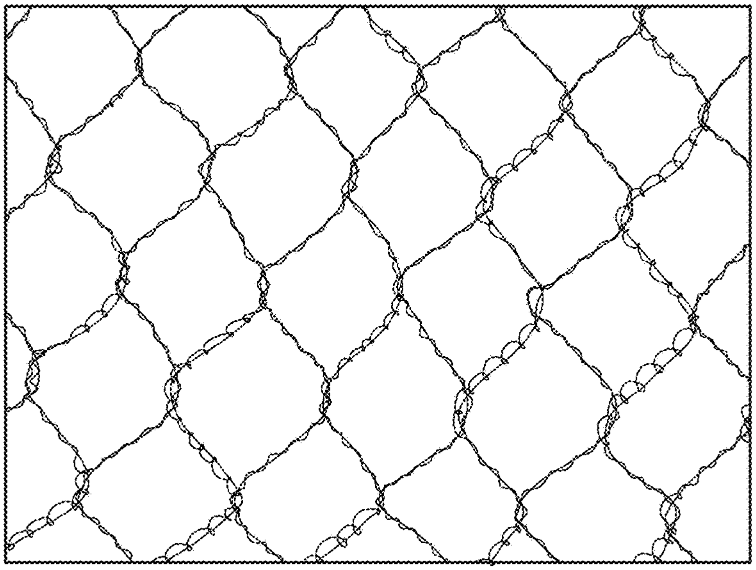
FIG. 8A shows an image of a mesh formed by a corner-locked stitch pattern, including corner-lock stitches at intersecting points. Between intersecting points, the threads are laid in a chain stitch configuration (the threads are looped), for illustration of variable stitching that may be used between corner locks.
Figure 8B:
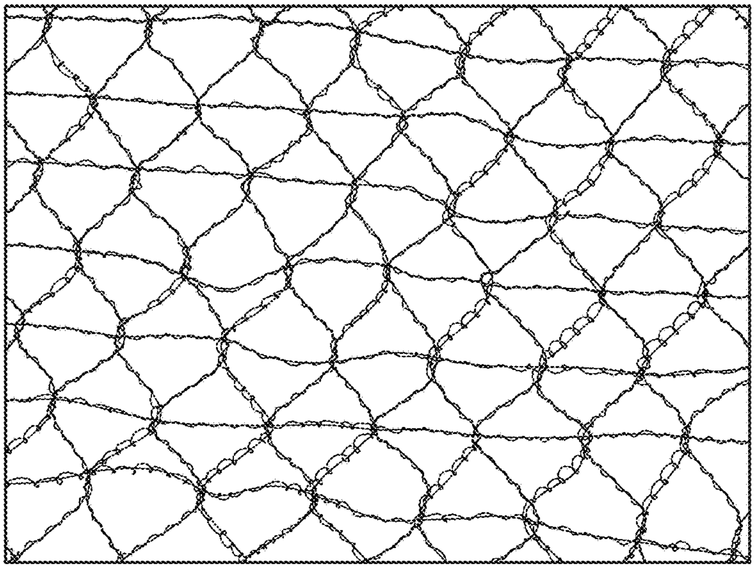
FIG. 8B shows an image of a variation of the mesh shown in FIG. 8A. In this variation, a straight stitch is further laid horizontally across each corner-lock.
Figure 8C:
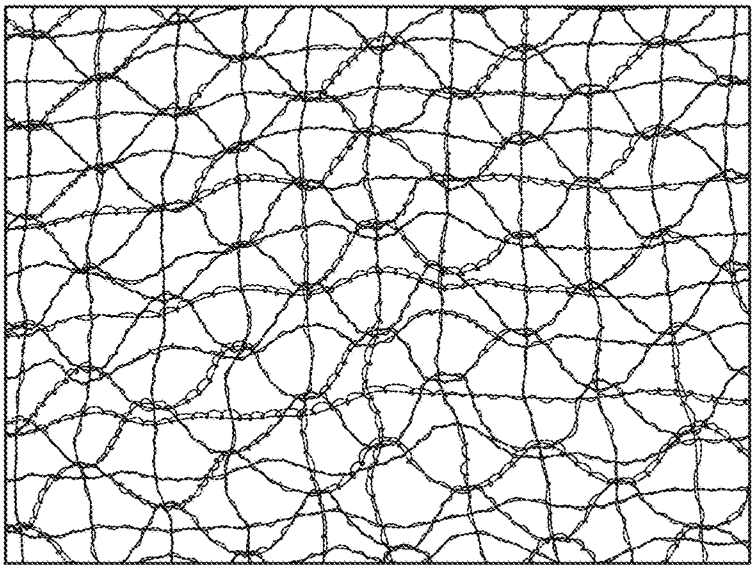
FIG. 8C shows an image of another variation of the mesh shown in FIG. 8A. In this variation, a second corner-locked stich pattern is laid on top of the first corner-locked stitch pattern. The second stitch pattern is oriented diagonally relative to the first stitch pattern.
Figure 9:
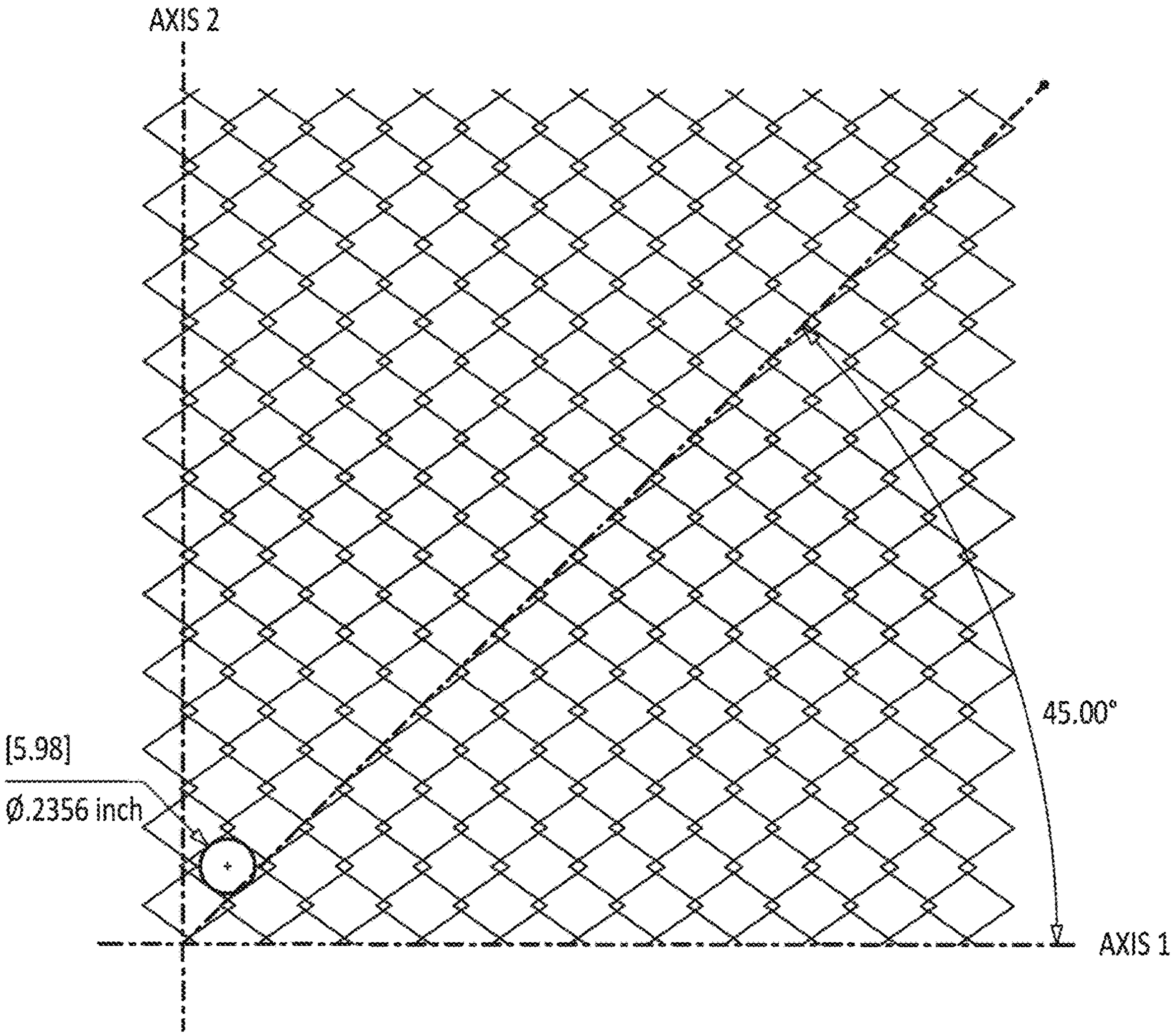
FIG. 9 shows an example of a mesh built upon a corner-lock stitch pattern. The mesh is shown in a liner X-Y plane. The pores are oriented in a parallelogram-like configuration, laid at about a 45 degree angle.
Figure 10:
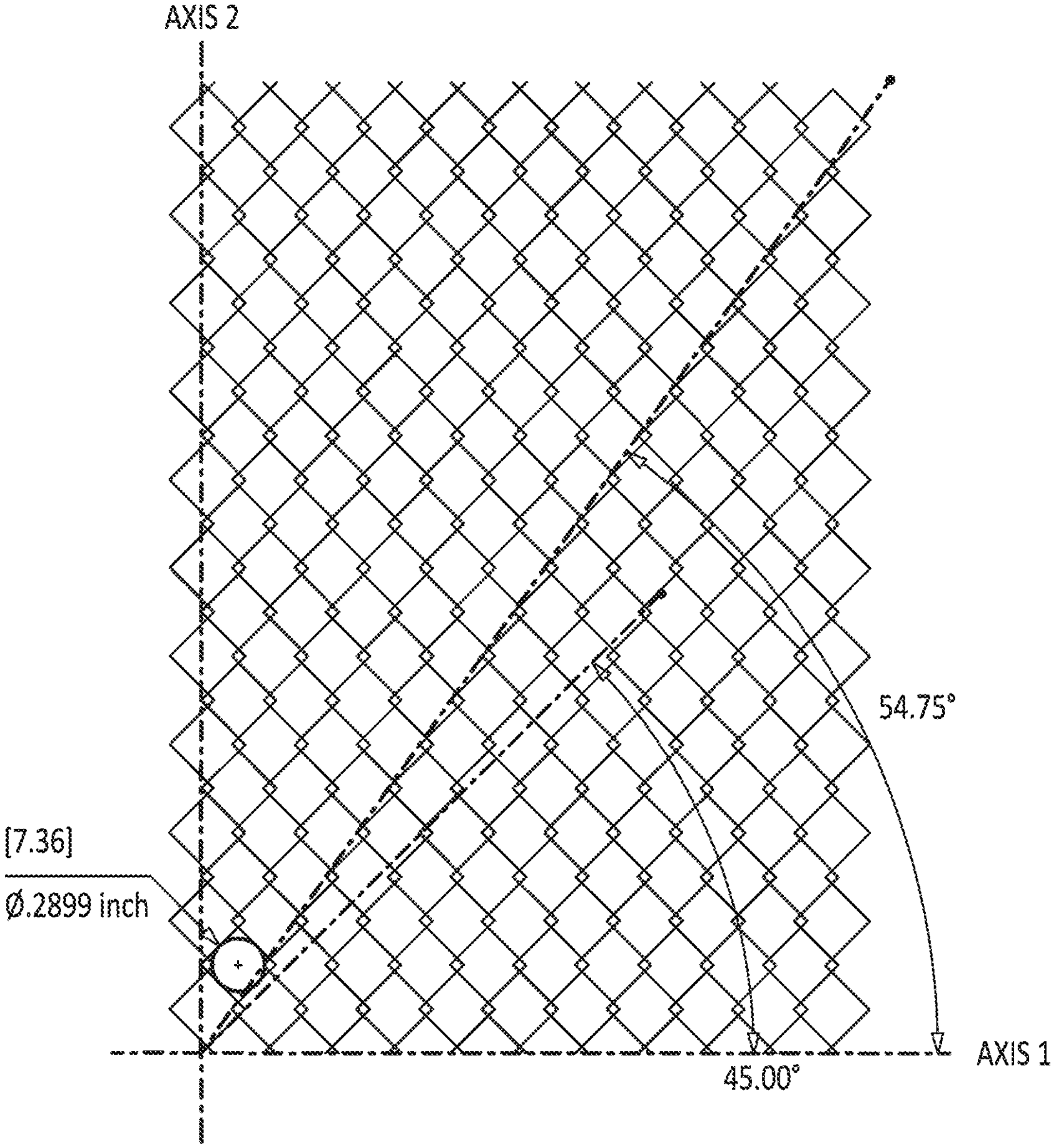
FIG. 10 shows another example of a mesh built upon a corner-lock stitch pattern. The mesh is shown in a liner X-Y plane. The pores are oriented in a parallelogram-like configuration, laid at about a 55 degree angle.
Figure 11:
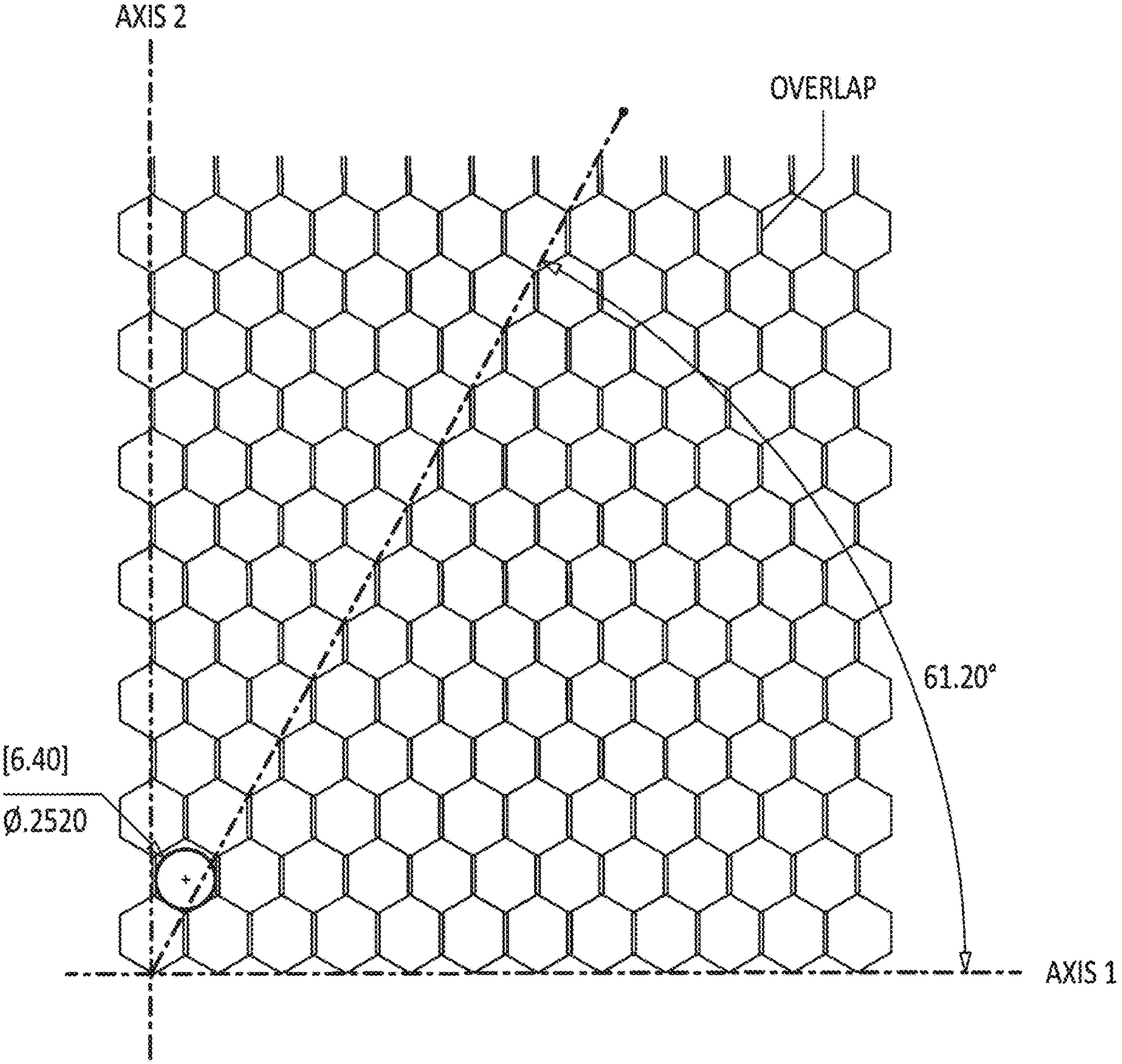
FIG. 11 shows another example of a mesh built upon a corner-lock stitch pattern. The mesh is shown in a liner X-Y plane. The pores are oriented in a hexagonal, honey-comb-like configuration, laid at about a 61 degree angle.

A mesh comprises a plurality of pores, or interstices between overlapping threads or yarns, which overlapping threads or yarns may comprise stitched threads or yarns, and which may comprise corner-locked stitches. The corner-lock stitches may surround the pores, being at each corner about the pore shape. The pores may comprise any suitable shape or dimension, or any suitable combination of shapes and/or dimensions. The pores may comprise one or more of a circular or elliptical shape, a square, diamond, parallelogram, or rhomboid shape, a rectangular shape, a triangular shape, a pentagonal shape, a hexagonal shape, a heptagonal shape, an octagonal shape, or other polygonal shape. Non-limiting examples of pore shapes are shown in FIG. 9 (diamond or rhomboid shape), FIG. 10 (square shape), and FIG. 11 (hexagonal shape). The pores may be arranged, for example, in rows, or in a concentric pattern, or in a random pattern. The pores may overlap (e.g., FIG. 11). The pores may be open, or may comprise crossing patterns that span one or more dimensions within the pore (See, e.g., FIGS. 8B and 8C). Such crossing patterns may comprise overlapping zigzag stitches, including corner-locked stitches.

The pores may comprise any suitable length, width, or diameter dimensions. Such dimensions may be from about 0.1 mm to about 10 mm. The dimensions may be from about 0.5 mm to about 5 mm, from about 0.5 mm to about 10 mm, from about 1 mm to about 10 mm, from about 1 mm to about 8 mm, from about 1 mm to about 7 mm, from about 1 mm to about 5 mm, from about 1 mm to about 3 mm, from about 1 mm to about 2 mm, from about 3 mm to about 9 mm, from about 3 mm to about 7 mm, from about 3 mm to about 5 mm, from about 4 mm to about 10 mm, from about 4 mm to about 8 mm, from about 4 mm to about 6 mm, from about 5 mm to about 10 mm, from about 6 mm to about 10 mm, from about 7 mm to about 10 mm, from about 8 mm to about 10 mm, or from about 9 mm to about 10 mm.

A corner-lock stitch pattern may be sewn or embroidered into or onto a substrate. The substrate may be any material into which filaments, yarns, or threads may be sewn into a corner-lock stitch pattern according to this disclosure. The substrate may itself comprise a mesh, such that in some aspects, a substrate mesh may comprise a mesh comprising a corner-lock stitch pattern sewn or embroidered into the substrate mesh. A substrate material may be a natural or synthetic material, may be a textile, and may be woven or non-woven. The substrate or the substrate material may have any thickness, or length and width dimensions. Non-limiting examples of substrate materials include cloth or fabric, lace, leather, silk, linen, nylon, polyester, polypropylene, polyethylene, cotton, satin, wool, bamboo, cashmere, jute, burlap, fleece, felt, spandex, rayon, denim, and other suitable materials, or any combination thereof. In some preferred aspects, the substrate material is a biotextile or a medical textile. Biotextiles or medical textiles may be implantable in or on the human body.

Biotextiles include biocompatible materials, which may be obtained or derived from living tissue. Living tissue includes, for example dermis/skin tissue (and sub-tissue, extracellular matrices), pericardium, peritoneum, intestine, stomach, forestomach, and other suitable tissues. The animal source may be any suitable animal, including a human, pig, cow, or sheep, or may be synthesized, for example, by recombinant expression. Biotextiles may be biodegradable or resorbable. Some non-limiting examples of biotextiles include extracellular matrix-derived tissue scaffolds, autograft tissue, allograft tissue, and xenograft tissue, as well as artificial skin, artificial heart valves, and other implantable prosthetics. Medical textiles include biocompatible materials, which may include synthetic materials. Some non-limiting examples of medical textiles include hernia repair meshes or materials, which may comprise polypropylene, polyethylene, and other implantable prosthetics.

The yarn or threads used to stitch materials and create the substrate, and/or the corner-locked stitches and meshes may be made of any suitable material, and may comprise any suitable weight. The yarn or thread may comprise monofilament yarn or thread, or multi-filament yarn or thread. The thread weight may be a function of the purpose to which the corner-locked mesh is used. The thread weight may range from about 20 weight to about 120 weight. The thread may comprise a denier of from about 1 denier to about 2000 denier. The thread may comprise a denier of at least about 20-denier. The thread may comprise a denier of at least about 30-denier. The thread may comprise a denier of at least about 40-denier. The thread may comprise a denier of at least about 50-denier. The thread may comprise a denier of at least about 60-denier. The thread may comprise a denier of at least about 70-denier. The thread may comprise a denier of at least about 80-denier. The thread may comprise a denier of at least about 90-denier. The thread may comprise a denier of at least about 100-denier. The thread may comprise a denier of at least about 120-denier. The thread may comprise a denier of at least about 150-denier. The thread may comprise a denier of at least about 200-denier. The thread may comprise a denier of at least about 250-denier. The thread may comprise a denier of at least about 300-denier. The thread may comprise a denier of at least about 400-denier. The thread may comprise a denier of at least about 500-denier. The thread may comprise a denier of at least about 600-denier. The thread may comprise a denier of at least about 700-denier.

The yarn may comprise plied yarn or twisted yarn (e.g., z twist or s twist). The thread material may comprise a natural fiber, such as cotton, wool, silk, or other natural material, or may comprise a synthetic fiber such as polyester, nylon, polypropylene, rayon, or other synthetic material. The thread may comprise a continuous filament. The thread may comprise a monofilament. The thread may comprise a staple filament. The thread material may comprise a metal. The thread may comprise a wire, for example, a polymeric wire, composite wire, or metal wire. The thread material preferably is biocompatible and, in some aspects, is resorbable. The thread material may comprise a polydioxanone, polycarbonate, polyurethane, poly(alpha-ester), polyglycolide, polylactide (e.g., poly(L-lactic acid), poly(D-lactic acid), and poly(D,L-lactic acid), poly(4-hydroxybutyric acid)—which is a homopolymer of 4-hydroxybutyrate (4HB), and belongs to a diverse class of materials called polyhydroxyalkanoates (PHAs)—and poly(lactide-co-glycolide)), polycaprolactone, polypropylene, polyester, poly (propylene fumarate), polyanhhydride, polyacetal, polycarbonate (e.g., poly(trimethylene carbonate)), poly(ortho ester), polyphosphazene, polyphosphoester, polytetrafluoroethylene, polyethylene terephthalate, or any combination or co-polymer thereof. Polypropylene, polyester, and polyethylene are preferred, with monofilament polyethylene more preferred.

The yarn or thread may be colored. Colors may indicate a proper orientation of the mesh or material+mesh, for example, the colors may indicate the proper orientation for implantation of a hernia repair mesh. Colors may indicate a front or back.

Between corner-locks, the thread may further comprise other stitch patterns, including a chain stitch, Merrow stitch, lock stitch, zigzag stitch, straight stitch, running stitch, back stitch, satin stitch, or combinations thereof, or any other suitable stitch types. Such patterns may serve, for example, to further strengthen the mesh, or may be decorative.

The following Example is provided to describe corner-lock stitch pattern qualities in greater detail. The Example is intended to illustrate, not to limit.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as “under”, “below”, “lower”, “over”, “upper” and the like, may be used herein for ease of description to describe one element or feature’s relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as “under” or “beneath” other elements or features would then be oriented “over” the other elements or features. Thus, the exemplary term “under” can encompass both an orientation of over and under. The device may be otherwise oriented (rotated 90 degrees or at other orientations) and the spatially relative descriptors used herein interpreted accordingly. Similarly, the terms “upwardly”, “downwardly”, “vertical”, “horizontal” and the like are used herein for the purpose of explanation only unless specifically indicated otherwise.

Although the terms “first” and “second” may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word “comprise”, and variations such as “comprises” and “comprising” means various components can be co-jointly employed in the methods and articles (e.g., compositions and apparatuses including device and methods). For example, the term “comprising” will be understood to imply the inclusion of any stated elements or steps but not the exclusion of any other elements or steps.

As used herein in the specification and claims, including as used in the examples and unless otherwise expressly specified, all numbers may be read as if prefaced by the word “about” or “approximately,” even if the term does not expressly appear. The phrase “about” or “approximately” may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value “10” is disclosed, then “about 10” is also disclosed. Any numerical range recited herein is intended to include all sub-ranges subsumed therein. It is also understood that when a value is disclosed that “less than or equal to” the value, “greater than or equal to the value” and possible ranges between values are also disclosed, as appropriately understood by the skilled artisan. For example, if the value “X” is disclosed the “less than or equal to X” as well as “greater than or equal to X” (e.g., where X is a numerical value) is also disclosed. It is also understood that the throughout the application, data is provided in a number of different formats, and that this data, represents endpoints and starting points, and ranges for any combination of the data points. For example, if a particular data point “10” and a particular data point “15” are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term “invention” merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

Example 1

Compliance and Strength of Corner-Lock Stitch Patterns

Figure 13:
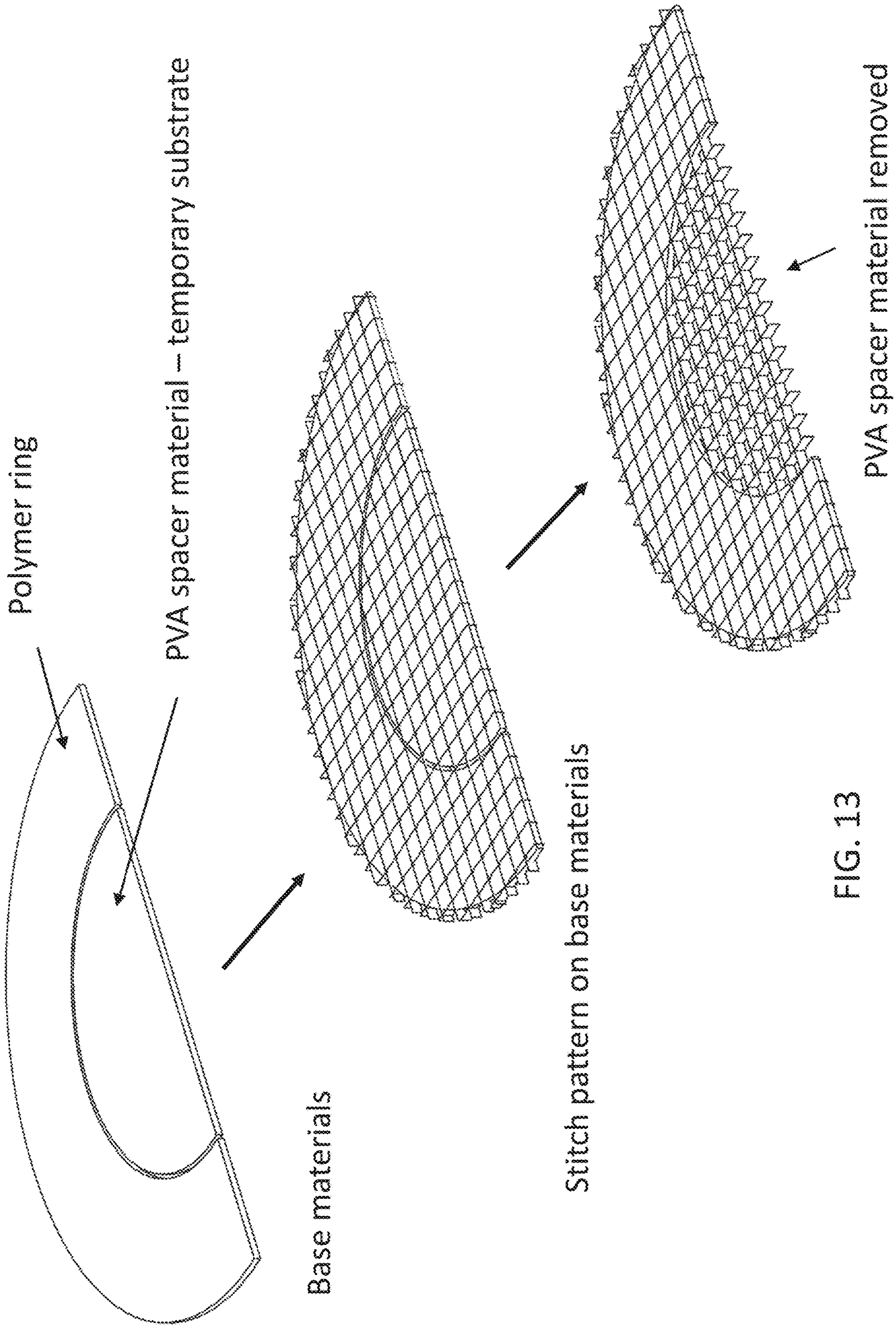
FIG. 13 illustrates construction of a stitch pattern (corner-lock stitch, or comparative standard straight grid stitch) onto a substrate. As shown in a cut-away, half view, a substrate comprised of a center of PVA and a perimeter of insoluble polymer is provided, and the desired stitch pattern is sewn into each of the PVA and insoluble polymer. Once the stitch pattern is laid, the PVA center is dissolved away, leaving behind a free mesh in the center.
Figure 14:
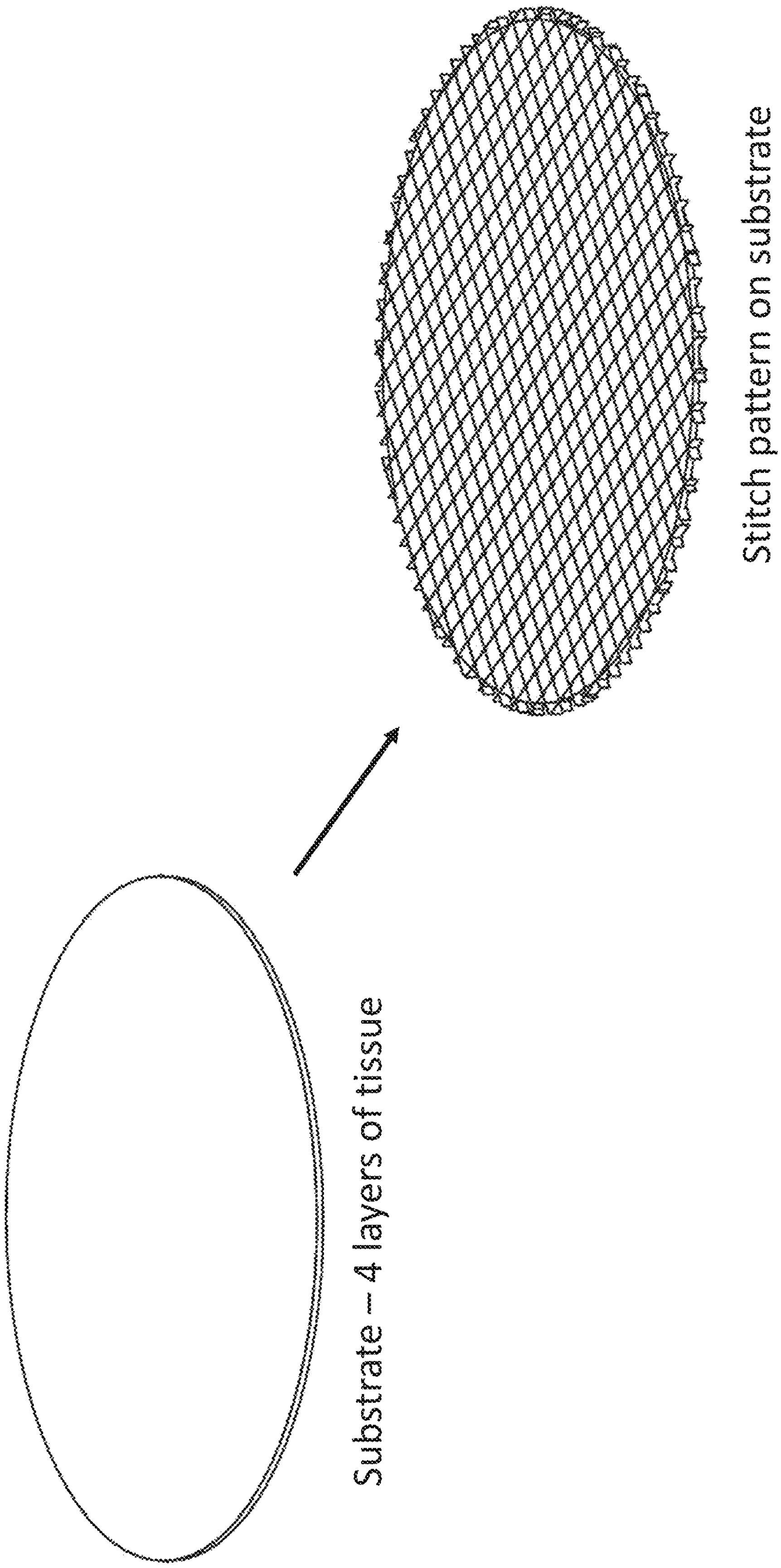
FIG. 14 shows construction of a stitch pattern onto an Endoform Reconstructive Template (ERT), a biotextile, substrate.

A corner-lock stitch pattern of polyethylene or polypropylene monofilament threads was embroidered onto a circular substrate comprising a polytetrafluoroethylene (PTFE) external ring (included as a frame, and not to test properties of the stitches sewn into it), and a polyvinyl alcohol (PVA) internal ring (FIG. 13). In parallel, a standard straight lock-stitch pattern (e.g., FIG. 2, no corner locks) was also embroidered into a PTFE/PVA substrate (FIG. 13). Following completion of each type of pattern, the PVA portion of substrate was dissolved away with water, leaving behind an embroidered corner-lock stitch pattern mesh unaffixed to any substrate in the center and also affixed around the perimeter to the insoluble portion of the substrate. Also in parallel, each of corner-lock and comparative straight-lock stitch patterns were embroidered into a four-layer extracellular matrix biotextile substrate, with the substrate not being dissolved away (FIG. 14). The test samples are summarized in Table 1 (variables: polypropylene (PP) and high strength polyethylene (PE) monofilaments used for embroidery, with corner-lock or standard straight stitch patterns, on either a 4-layer biotextile substrate or without substrate; Both stitch patterns had a similar pore size of about 3 mm).

TABLE 1

| Test sample arrays | | | | | | |
|---|---|---|---|---|---|---|
| Type | Corner-Lock Mesh | Straight-Lock Mesh | Polypropylene (PP) Monofilament | High-Strength Polyethylene (PE) Monofilament | Substrate-4 layers | No substrate |
| A | | X | X | | | X |
| B | | X | | X | | X |
| C | X | | X | | | X |
| D | X | | | X | | X |
| E | | X | X | | X | |
| F | | X | | X | X | |
| G | X | | X | | X | |
| H | X | | | X | X | |

Figure 15:
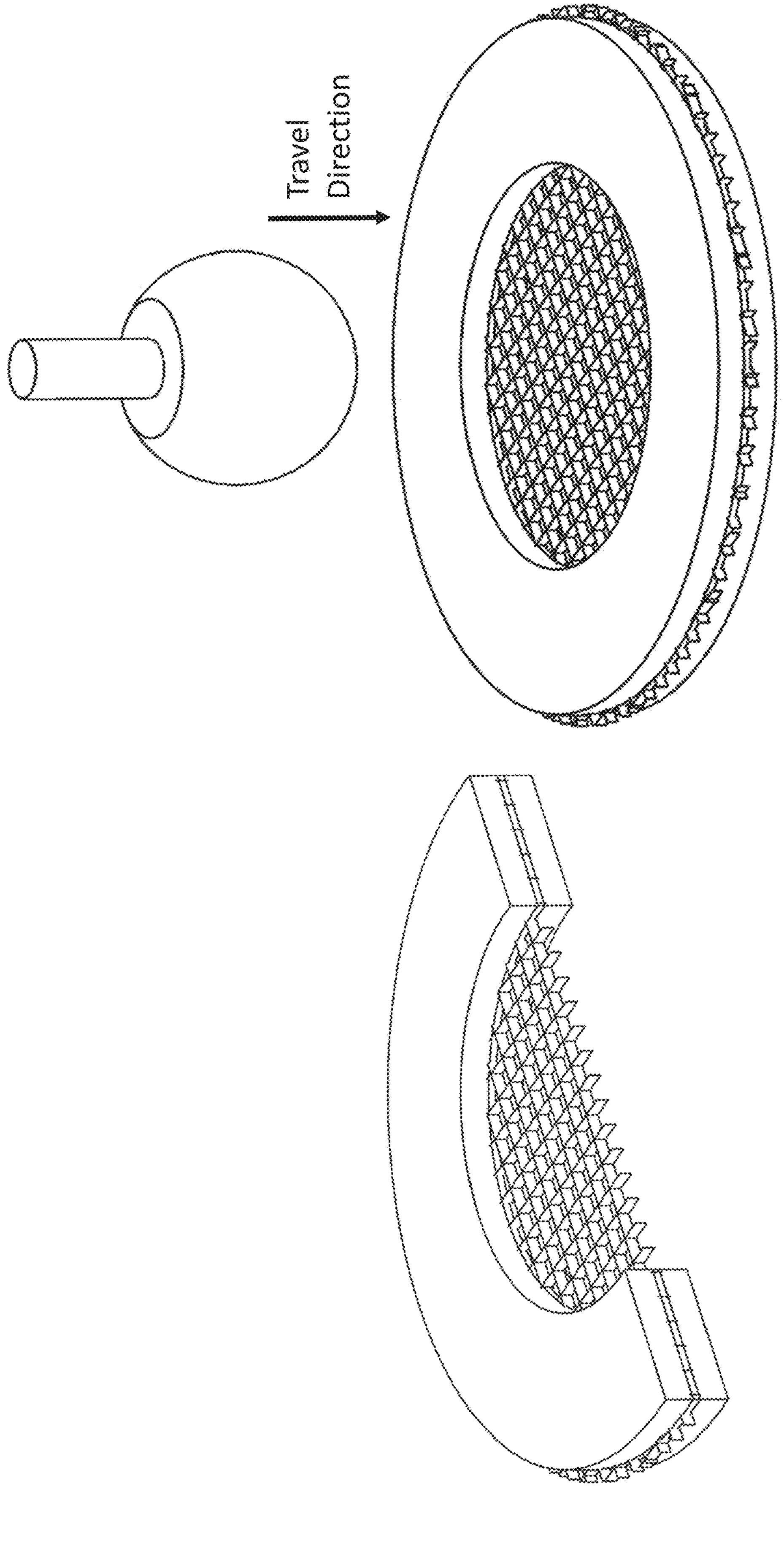
FIG. 15 illustrates how the ball burst test is carried out, with a mesh (with or without an underlying substrate) placed into a clamp, and then with a steel ball forced through the mesh.

Each of the stitch patterns (+/−substrate) were studied for strength and compliance (compliance is a function of, among other things, strength, stress, elongation, rebound, deformability, and elasticity properties of the particular materials or combination of materials) using the Ball Burst test method. The Ball Burst test method is used in the art to measure the force required to rupture a textile, by forcing a 1 inch diameter polished steel ball through a 1.75 inch inner-diameter textile ring at a constant rate of extension, 12 inch/minute (ASTM D767-07 (Reapproved 2011)). The Ball Burst tests were conducted on each stitch pattern (+/− substrate) on an Instron Model 3345 Single column Tensile Tester with ball burst ring clamps and fixture (FIG. 15).

Figure 16:
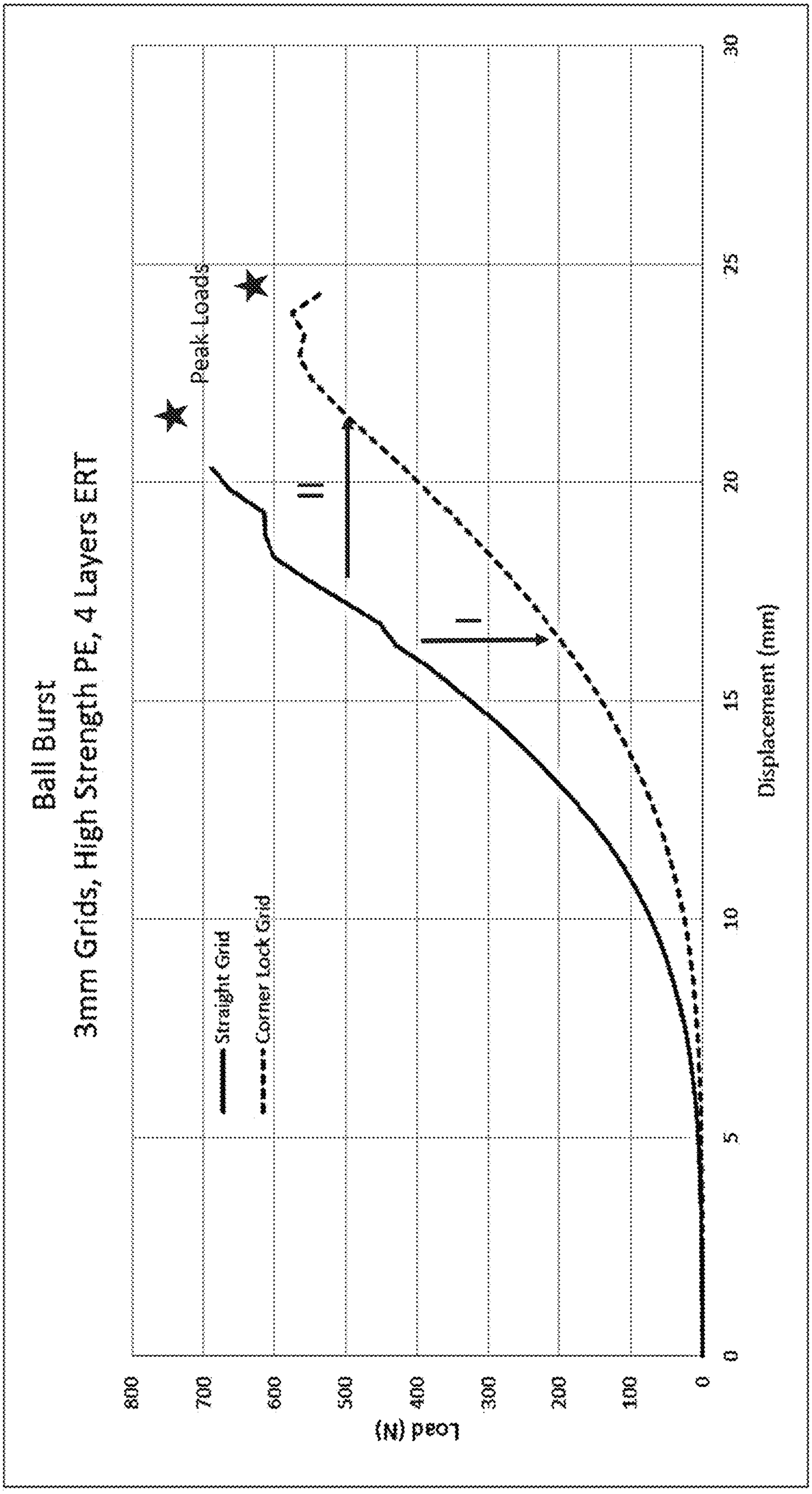
FIG. 16 shows the results of a ball burst compliance test on a polyethylene mesh sewn as a corner-lock stitch pattern (dotted line) or a straight stitch pattern (solid line) into a four-layer ERT substrate. The chart shows force versus displacement.
Figure 17:
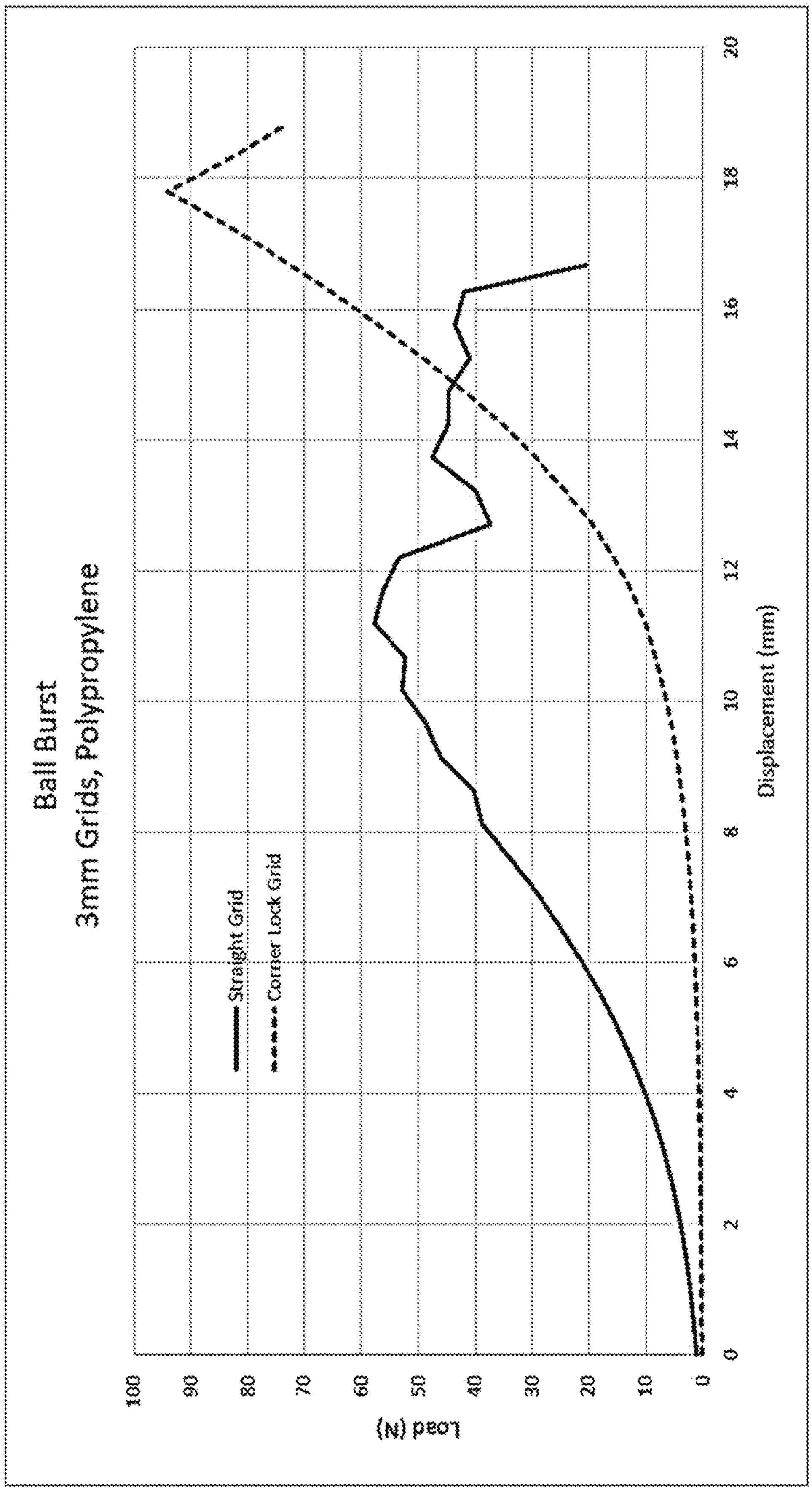
FIG. 17 shows the results of a ball burst compliance test on a polypropylene mesh sewn as a corner-lock stitch pattern (dotted line) or a straight stitch pattern (solid line), without a substrate. The chart shows force versus displacement.
Figure 18:
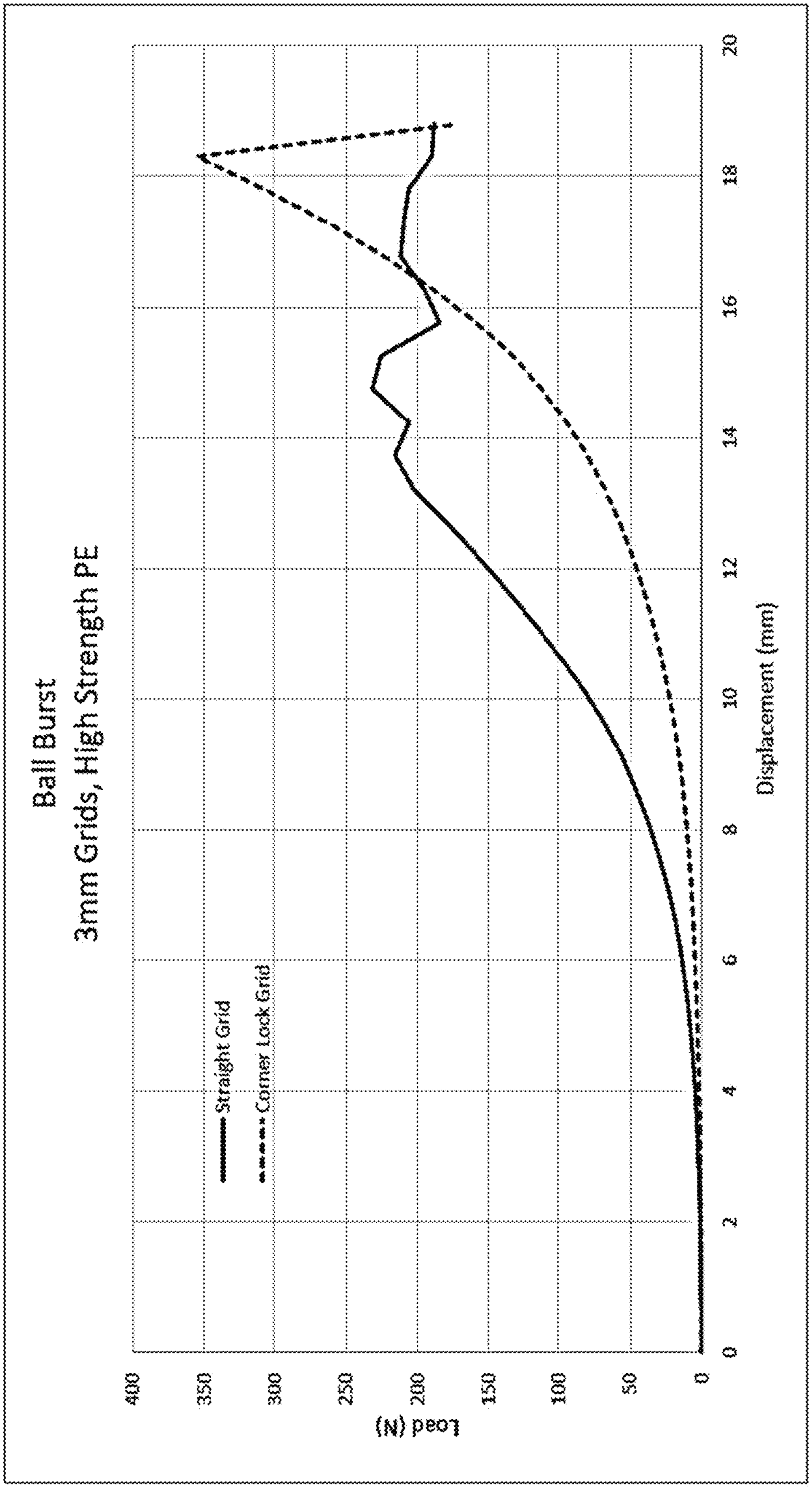
FIG. 18 shows the results of a ball burst compliance test on a polyethylene mesh sewn as a corner-lock stitch pattern (dotted line) or a straight stitch pattern (solid line), without a substrate. The chart shows force versus displacement.

Compliance control tests are charted in FIGS. 16 through 18. FIG. 16 graphs Force (N) vs. Displacement (in mm) data for 2 samples (Type E and G, Table 1), highlighting the compliance difference between the different grid patterns for embroidered tissue. Direction Arrow I shows how, for a given displacement, the corner-lock grid pattern offers less resistance than the standard straight grid pattern. Direction Arrow II shows how, for a given resistance load, the corner-lock stitch patterns allows more ball travel distance than the straight stitch pattern. This illustrates how the corner-lock grid pattern is more compliant than a straight grid pattern, with each pattern made of the same material (high strength PE in FIG. 16) and with similar pore dimensions. FIGS. 17 (PP) and 18 (high strength PE) illustrate this same relationship where the corner-lock stitch pattern and straight stitch pattern were without a substrate samples (Table 1, Type A-D). The data show that the corner-lock stitch pattern is more compliant than the straight-stitch pattern, whether or not a substrate underlies the pattern, and regardless of the stitch pattern thread material. Of note, it was observed that manipulation of the shape and type of the corner-lock stitch patterns allows for modulation (greater or lesser) of the compliance (not shown).

Figure 19:
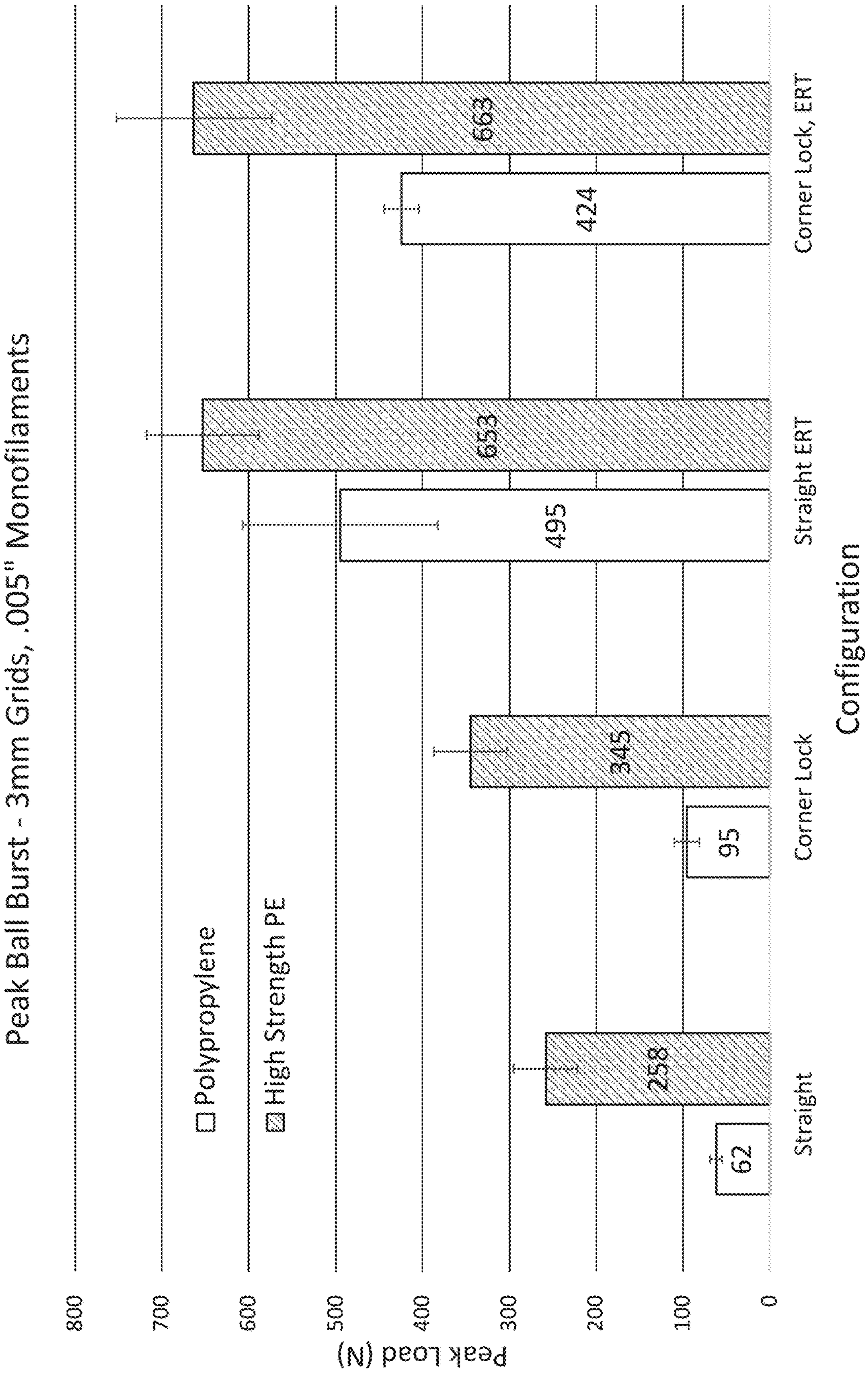
FIG. 19 shows a bar graph comparing a ball burst strength test carried out using 0.005 inch monofilament thread corner lock or straight stitch patterns, either with a four layer ERT substrate or without a substrate. Peak load (N) was measured.

Strength tests are summarized in FIG. 19. FIG. 19 shows, for the same size monofilament, the difference between PP and PE materials using averaged Ball Burst peak loads. N-values are either 4 or 6 samples per type. In every paired configuration, the average peak load for the PE was observed to be higher than the average peak load for PP. In the chart, corner-lock versus standard straight stitch patterns, formed of PP or PE, on either a 4-layer biotextile substrate or without a substrate (stitched into PVA that was dissolved away to leave behind the stitch pattern mesh) are compared for their strength. As shown, high strength polyethylene monofilament threads (0.005" monofilament) exhibited higher strength characteristics than polypropylene monofilament threads (0.005" monofilament) in both straight and corner-lock stitch patterns. In general, corner-lock stitch patterns were found to exhibit higher strength characteristics than standard straight stitch patterns.

The disclosure is not limited to the embodiments described and exemplified above, but is capable of variation and modification within the scope of the appended claims.

What is claimed is:

1. An implant, comprising:

a substrate comprising a biocompatible material; and a reinforcing mesh sewn into the substrate, the reinforcing mesh including a corner-stitch pattern comprising:

a first lock-stitch pattern including a first upper thread and a first lower thread that interlace at a first thread interlace point; and a second lock-stitch pattern including a second upper thread and a second lower thread that interlace at a second thread interlace point, wherein the second lock-stitch pattern overlaps the first lock-stitch pattern such that the second upper thread and the second lower thread envelop the first upper thread and the first lower thread adjacent to the first thread interlace point and the second thread interlace point.

2. The implant of claim 1, further comprising a straight stitch laid across the first and second lock-stitch patterns.

3. The implant of claim 1, wherein the overlapping first and second lock-stitch patterns form a rectangular or square pattern.

4. The implant of claim 1, wherein the first upper thread and the first lower thread are sandwiched between the second upper thread and the second lower thread.

5. The implant of claim 1, wherein the substrate includes multiple layers.

6. The implant of claim 1, wherein the biocompatible material comprises an extracellular matrix.

7. The implant of claim 1, wherein the biocompatible material comprises a polymer mesh, wherein the polymer mesh comprises a polymer selected from the group consisting of polydioxanone, polycarbonate, polyurethane, poly (alpha-ester), polyglycolide, poly(L-lactic acid), poly(D-lactic acid), poly(D,L-lactic acid), poly(4-hydroxybutyric acid), polycaprolactone, polyethylene, polypropylene, polyester, poly(propylene fumarate), polyanhhydride, polyacetal, poly(ortho ester), polyphosphazene, polyphosphoester, polytetrafluoroethylene, and polyethylene terephthalate.

8. The implant of claim 1, wherein the first and second upper threads and the first and second lower threads comprise a resorbable material.

9. The implant of claim 1, wherein each of the first and second lock-stitch patterns comprises one or more curves, one or more angles, or a combination of one or more curves and angles.

10. The implant of claim 1, wherein interstices between the first and second lock-stitch patterns have a length, width or diameter ranging from about 0.1 mm to about 10 mm.

11. The implant of claim 1, wherein one or more of the first upper thread, the first lower thread, the second upper thread, and the second lower thread comprises a monofilament yarn or a multifilament yarn.

12. The implant of claim 1, wherein the implant is a hernia repair implant.

13. An implant, comprising:

a substrate comprising a biocompatible material; and a reinforcing mesh sewn into the substrate, the reinforcing mesh including:

a corner-stitch pattern comprising:

a first lock-stitch pattern including a first upper thread and a first lower thread that are interlaced at first thread interlace points; and a second lock-stitch pattern including a second upper thread and a second lower thread that are interlaced at second thread interlace points, wherein the second lock-stitch pattern overlaps the first lock-stitch pattern such that the second upper thread and the second lower thread envelop the first upper thread and the first lower thread adjacent to the at least one of the first thread interlace points and at least one of the second thread interlace points; and a straight stitch laid across the first and second lock-stitch patterns.

14. The implant of claim 13, wherein the first and second upper threads and the first and second lower threads comprise a resorbable material.

15. The implant of claim 13, wherein each of the first and second lock-stitch patterns comprises one or more curves, one or more angles, or a combination of one or more curves and angles.

16. The implant of claim 13, wherein interstices between the first and second lock-stitch patterns have a length, width or diameter ranging from about 0.1 mm to about 10 mm.

17. The implant of claim 13, wherein one or more of the first upper thread, the first lower thread, the second upper thread, and the second lower thread comprises a monofilament yarn or a multifilament yarn.

18. The implant of claim 13, wherein the implant is a hernia repair implant.

19. A method of forming an implant, the method comprising:

sewing a reinforcing mesh into a substrate, the substrate comprising a biocompatible material, wherein forming the reinforcing mesh comprises:

sewing a first lock-stitch pattern into the substrate, wherein the first lock-stitch pattern includes a first upper thread and a first lower thread that interlace at at least one first thread interlace point; and sewing a second lock-stitch pattern into the substrate, wherein the second lock-stitch pattern includes a second upper thread and a second lower thread that interlace at at least one second thread interlace point, wherein the second lock-stitch pattern overlaps the first lock-stitch pattern such that the second upper thread and the second lower thread envelop the first upper thread and the first lower thread adjacent to the at least one first thread interlace point and the at least one second thread interlace point.

20. The method of claim 19, further comprising sewing at least one straight stitch across the first and second lock-stitch patterns.

* * * * *